United States Patent [19]
Ichikawa et al.

[11] Patent Number: 6,039,732
[45] Date of Patent: *Mar. 21, 2000

[54] ELECTRIC OPERATION APPARATUS

[75] Inventors: Yoshito Ichikawa, Saitama-ken; Takashi Mihori, Hachioji; Tomohisa Sakurai, Sagamihara; Yoshitaka Honda, Tokorozawa, all of Japan

[73] Assignee: Olympus Optical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/631,272

[22] Filed: Apr. 12, 1996

[30] Foreign Application Priority Data

| Apr. 18, 1995 | [JP] | Japan | 7-092706 |
| May 1, 1995 | [JP] | Japan | 7-107508 |
| May 24, 1995 | [JP] | Japan | 7-125148 |
| May 16, 1995 | [JP] | Japan | 7-117521 |

[51] Int. Cl.$^7$ ............................................. A61B 17/36
[52] U.S. Cl. .................................... 606/38; 606/34
[58] Field of Search ............... 606/32–35, 37–42, 606/45–52

[56] References Cited

U.S. PATENT DOCUMENTS

| 4,196,734 | 4/1980 | Harris | 606/38 |
| 4,416,276 | 11/1983 | Newton et al. | |
| 4,416,277 | 11/1983 | Newton et al. | |
| 4,617,927 | 10/1986 | Manes | 606/38 |
| 4,658,819 | 4/1987 | Harris et al. | 606/38 |
| 4,727,874 | 3/1988 | Bowers et al. | 606/38 |
| 5,015,227 | 5/1991 | Broadwin et al. | 606/42 |
| 5,372,596 | 12/1994 | Klicek et al. | 606/34 |

FOREIGN PATENT DOCUMENTS

| 61-32016 | 7/1986 | Japan . |
| 64-76846 | 3/1989 | Japan . |
| 5-85177 | 12/1993 | Japan . |

*Primary Examiner*—David M. Shay
*Attorney, Agent, or Firm*—Frishauf, Holtz, Goodman, Langer & Chick, P.C.

[57] ABSTRACT

In an electric operation apparatus, a counter plate of a mono-polar type and a counter plate of a separate type are used to perform an electric operation. A counter plate connector connects a counter plate of a mono-polar type and a counter plate of a separate type. A first monitor is connected to the counter plate connector, and monitors the condition of the counter plate of the mono-polar type. A second monitor is connected to the counter plate connector, and monitors the condition of the counter plate of the separate type. A detector makes the first and second monitors operate on the basis of a predetermined operation procedure, thereby to detect the attachment conditions of the counter plates of respective types connected to the counter plate connector.

4 Claims, 26 Drawing Sheets

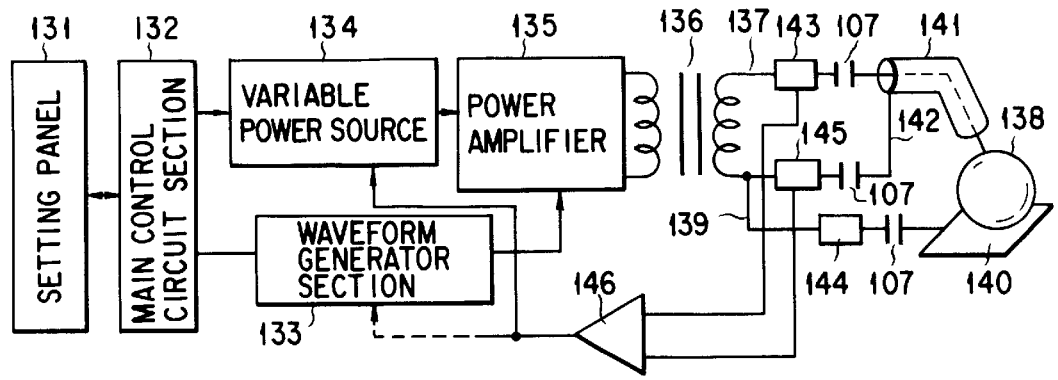
F I G. 10
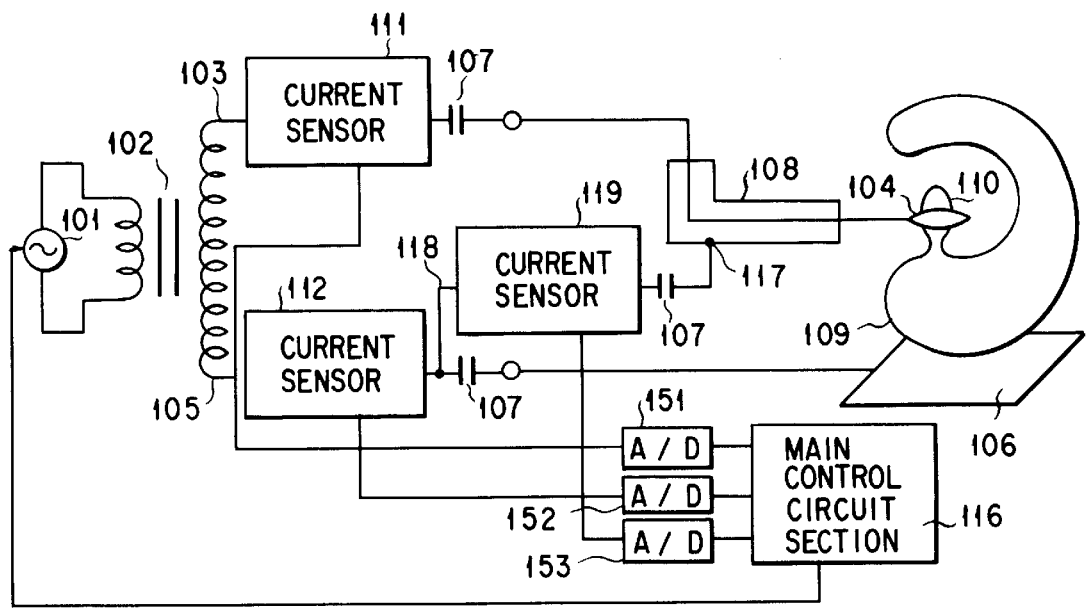
F I G. 11

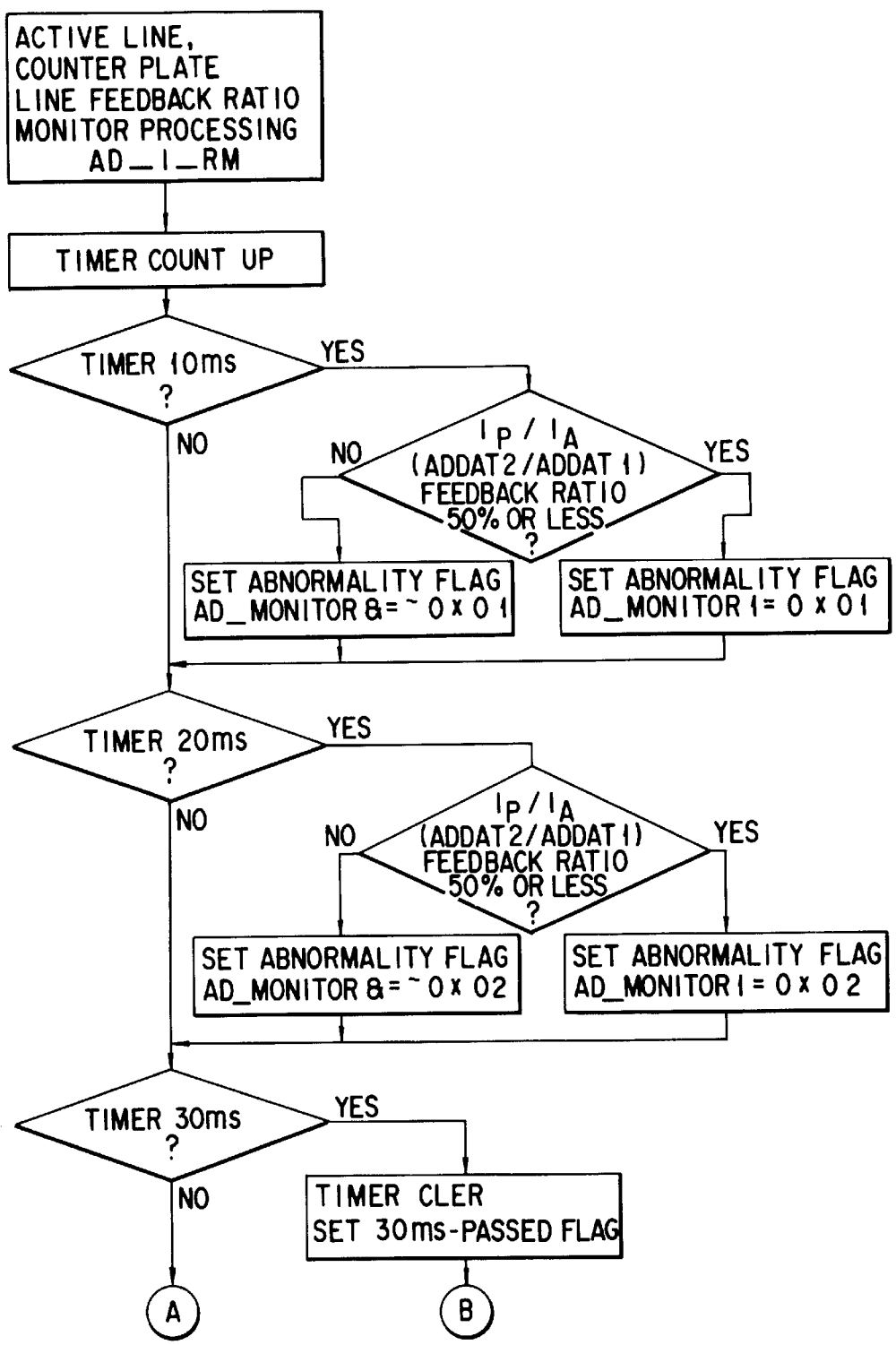
F I G. 14

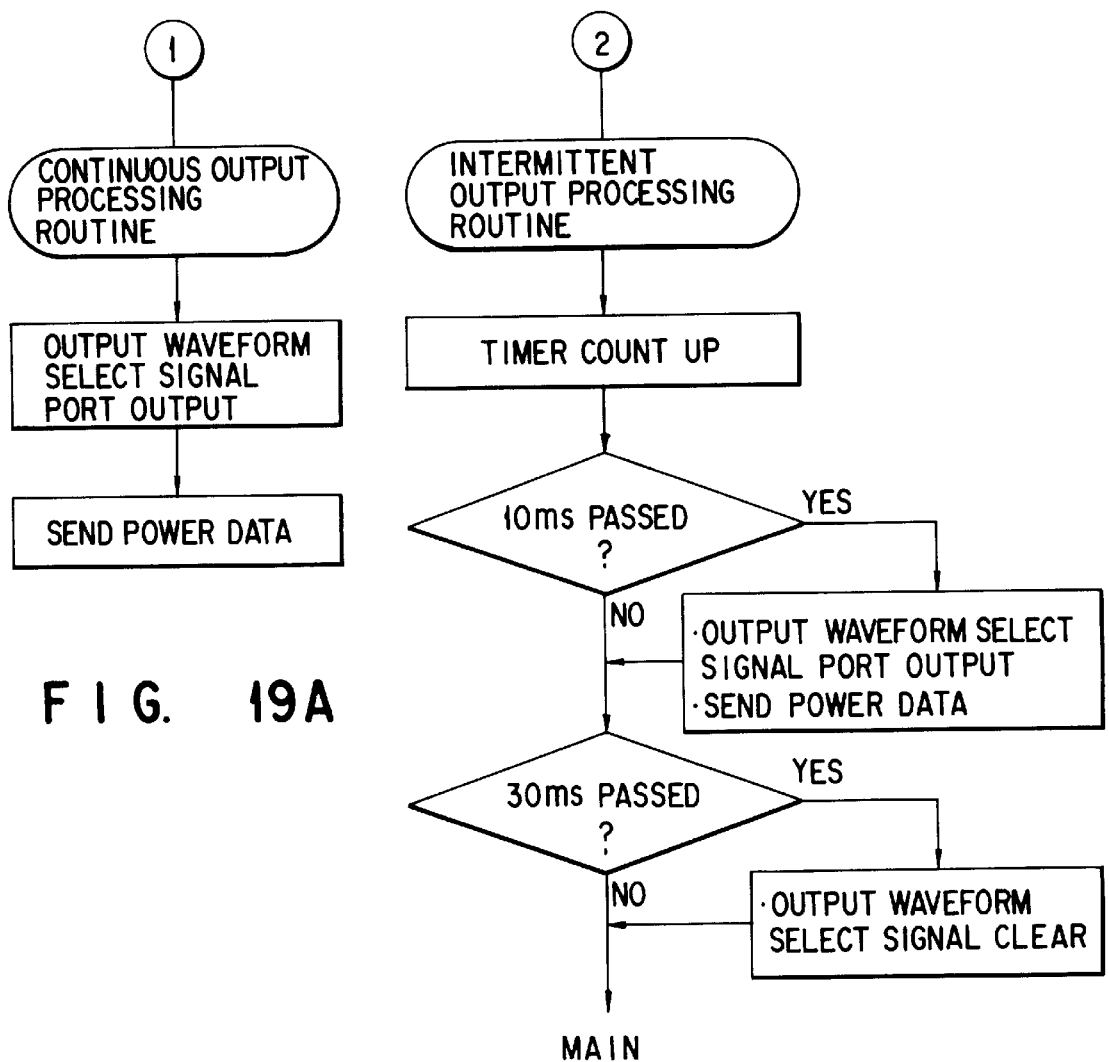
F I G. 19A
F I G. 19B

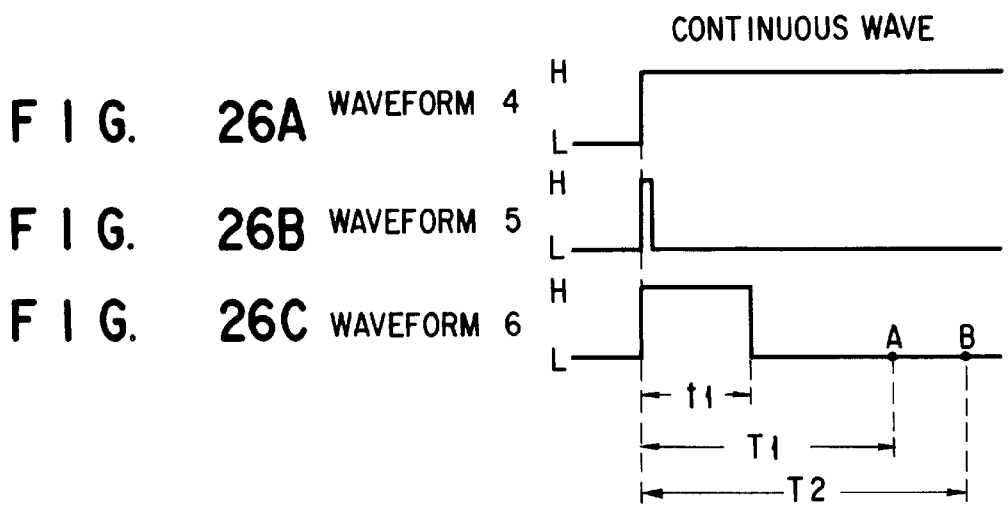
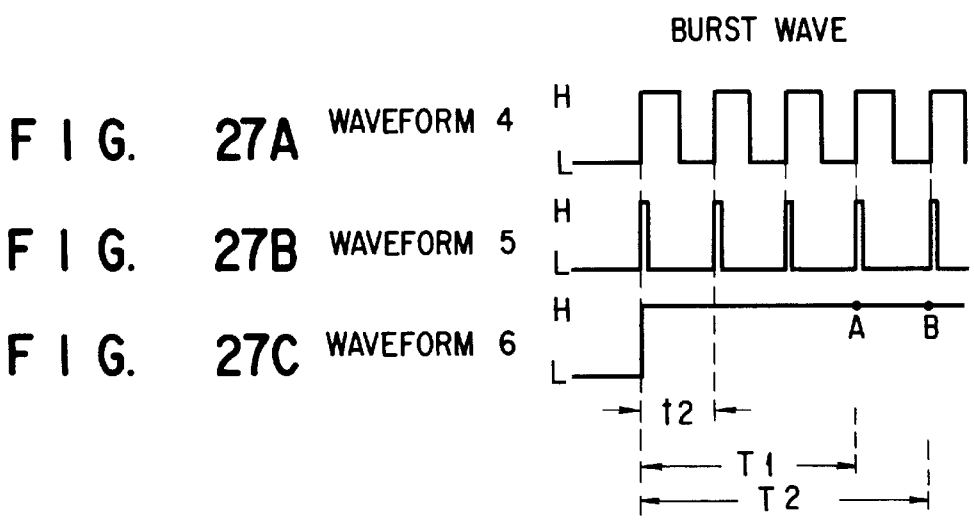
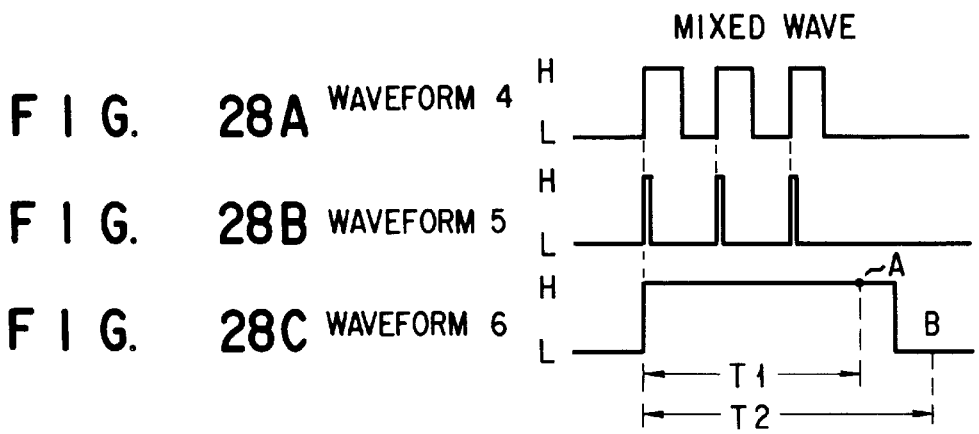

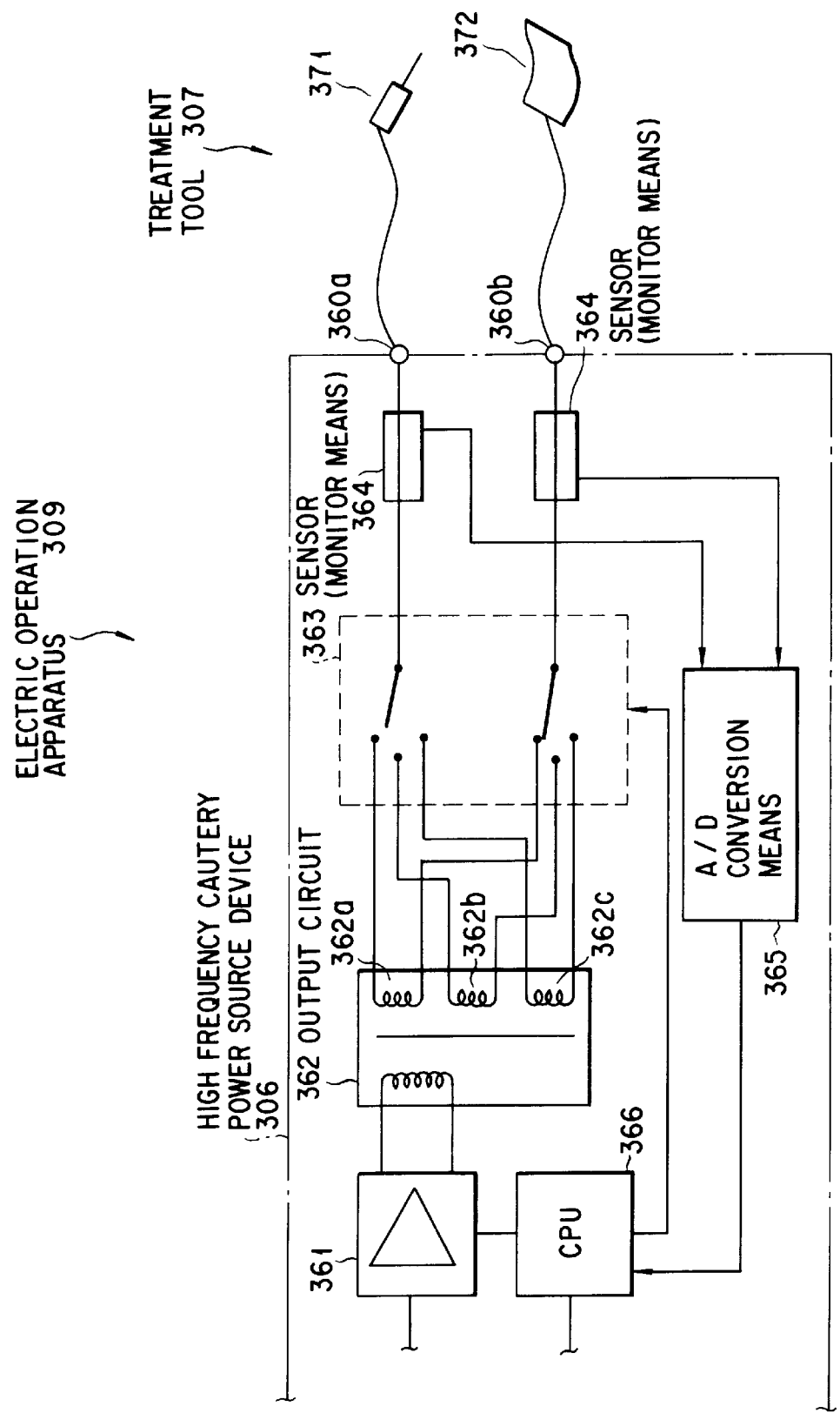
F I G. 29

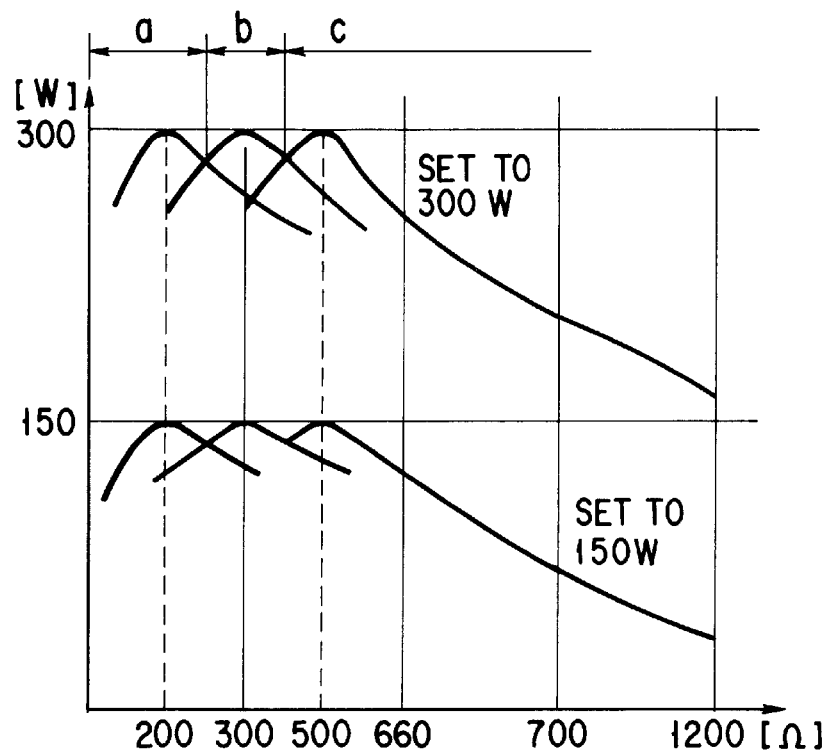
F I G. 30
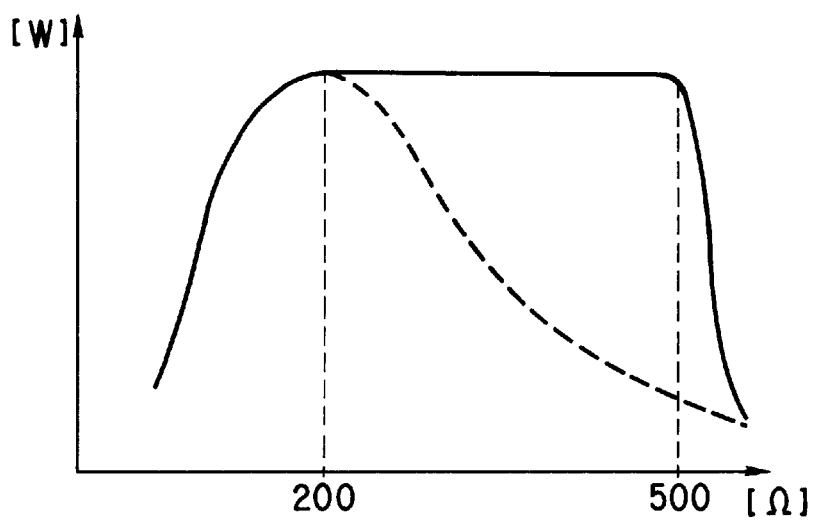
F I G. 31

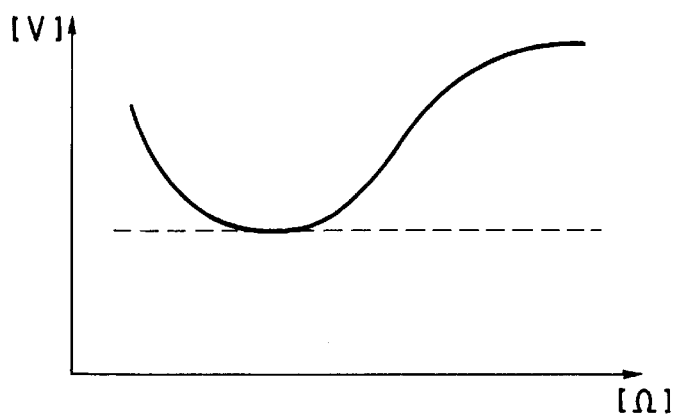
F I G. 32
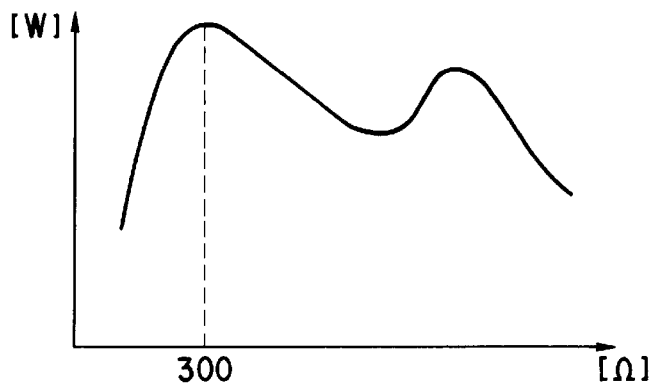
F I G. 33
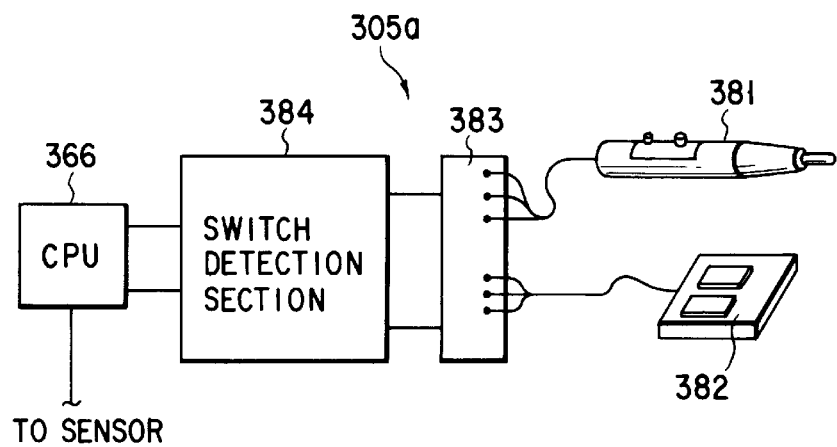
F I G. 34

ELECTRIC OPERATION APPARATUS

BACKGROUND OF THE INVENTION

1. Field of the Invention

The present invention relates to an electric operation apparatus, and particularly, to an electric knife which can immediately detect an undesirable situation for a patient and make a proper treatment responsive thereto, when an undesirable situation occurs in a surgical operation or a treatment using an endoscope.

2. Description of the Related Art

In surgical operations and treatments using an endoscope, it is important that operations and treatments are performed securely, and that safety is ensured for patients.

In the following, several conventional techniques will be explained which take into consideration such safety.

At first, a first conventional technique will be explained. For example, a mono-polar method is known as an output for an electric knife. According to this method a high frequency current outputted from a knife end is collected through an electrode called a counter electrode plate having a large area. A counter electrode plate is normally attached on body surfaces of a femoral region or buttocks of a patient, and is connected to the electric knife apparatus by a cable. In addition, when a situation occurs in which a high frequency current cannot be properly collected by the counter plate, a burn is caused at an undesirable portion, and therefore, a monitor circuit is provided to avoid such a situation.

Counter plates for an electric knife are roughly classified into two types. One of the types is a counter plate 403 of a mono-polar type, as shown in FIG. 1A, in which an 401 is provided with a sheet electrode 402, and in this counter plate 403, the electrode 402 is connected with two codes 404, thereby forming a loop.

Another type is a counter plate 407 of a separate type, as shown in FIG. 1B, in which two or more electrodes 406 are provided at intervals on a sheet 405 so as to form a sheet, and the electrodes 406 are respectively connected with codes 408. Respective electrodes 406 are attached to a patient, thereby to form a loop including the body surface of a patient.

As for a monitor circuit for detecting whether or not a counter plate is correctly attached, there have been methods which respectively correspond to the counter plates of the two types described above. Specifically, in a monitor circuit for a counter plate of a mono-polar type, a slight voltage is applied to a loop formed by two codes 404 and an electrode 402, and the continuity of a loop is detected, depending on whether or not a current flows, thereby to determine presence or absence of a disconnection of the codes 404 or a defective connection to an electric knife apparatus.

In addition, in a monitor circuit for a counter plate of a separate type, a slight direct current or alternating current is made flow between respecting electrodes 406, and the resistance or impedance between respective electrodes 406 is detected, thereby to determine the contact condition of the counter plate 407 with a patient.

Therefore, in order that both of the two types of counter plates 403 and 407 can be used, a conventional electric knife apparatus adopts a monitor circuit for a counter plate of a separate type, which has been modified to be applicable to a counter plate of a mono-polar type, and to be switched in accordance with the type of counter plate to be used. For example, there has been proposed a method in which the type of a counter plate is identified by making the shapes of connectors of the counter plates 403 and 407 different (cf. Japanese Patent Application KOKAI Publication No. 64-76846), and in which a user pushes selection switches corresponding to the counter plates.

Next, a second prior art technique will be explained. In general, in an electric knife apparatus, a high frequency of several hundreds KHz is used and theoretically, a high frequency current flows from an active line to an organic tissue. Then, this current is collected by the electric knife itself through a counter plate and patient codes. The high frequency current which has thus flowed through the route as described above functions to make a high frequency treatment effect.

However, since signals to be dealt with are of a high frequency as has been described above, a current flows to a route passing through the so-called ground under influences of a floating capacity in the air and a bonding capacity. There may be a case in which a leakage current of a high frequency which thus flows through the ground becomes a factor which causes an unintended burn in a patient or an operator.

In Japanese Patent Application KOKOKU Publication No. 61-32016, a safety system for an electric knife apparatus has been proposed which safely and securely performs a high frequency treatment. This is a system which detects a current IA flowing through an active line and a current IP fed back through a patient code from a counter plate, and which calculates a ratio of IP/IA. If the calculation result is lower than a predetermined value, this safety system determines that a high frequency leakage current has increased to a dangerous level, and controls the output.

Meanwhile, several electric knife apparatuses used in this kind of surgical operation comprise a spray coagulation function. The spray coagulation function means a technique in which a high voltage is applied between a treatment electrode portion and a patient tissue, with them kept apart from each other, thereby to obtain discharging, so that blood is coagulated. As a result of this, high coagulation performance can be effected at over a wide range of portions. Normally, to arrest bleeding, an electrode is brought into contact with a bleeding portion, and blood is coagulated by a heat effect of a high frequency current. In this case, blood or tissues may stick to the electrode portion, and the performance of an electric knife may be degraded. Otherwise, when the electrode is removed from tissues, a coagulating portion sticking to the electrode may be pealed off and may result in bleeding again.

However, since a coagulation treatment can be carried out with the electrode and tissues kept apart from each other in this kind of spray coagulation function, as has been described above, it is possible to overcome the above mentioned drawbacks which occur in normal blood coagulation.

Further, a third prior art technique will be explained. In recent years, an electric operation apparatus such as an electric knife utilizing a current of a high frequency (several hundreds kHz) and a high voltage (several hundreds to several thousands V) has been widely put into practical use. In an operation using this kind of electric operation apparatus, safety is particularly significant.

An electric operation apparatus using an electric knife utilizes various waveforms of high frequency signals, such as a continuous wave, a mixed wave, a burst wave, and the likes, in an operation. Substantially, these high frequency signal waveforms are previously stored in a memory device, and are extracted and used if necessary. Otherwise, high frequency signal waveforms are generated by a divider means, a counter, a multiplier means and the like, on the basis of a source generation signal. In addition, it is needless to say that high frequency signal waveforms can be generated by a combination of those methods.

In addition, in an electric operation apparatus using an electric knife, various high frequency signal waveforms are substantially outputted by one signal device.

Further, in view of the point that an electric knife is a device with a high voltage, as described above, the incision performance and coagulation performance have been improved. However, in order to detect whether or not a high frequency output of a predetermined power is obtained, a method has been taken in which a high frequency output (of several hundreds to several thousands V) is separated with use of an insulating means, and the result obtained therefrom is detected.

Next, a fourth prior art technique will be explained.

Conventionally, to perform incision or to arrest bleeding by coagulation, in a surgical or internal operation, an electric operation apparatus has been used. In this electric operation apparatus, since a high frequency cautery power source apparatus (which will be referred to as only a cautery power source hereinafter) is connected with a treatment tool, and a treatment is performed by outputting a high frequency power from the treatment tool to a portion to be treated, the high frequency power outputted from the cautery power source must be optimally controlled. Therefore, an output current outputted from a high frequency power source for an electric operation and a returning current are detected and compared with each other, to indirectly detect a leakage current or an impedance between the output end of the high frequency power source and the returning end. In addition, in this bipolar mode, a temperature sensor is formed at the top end of an electrode, to detect the temperature added to a tissue surface.

However, even if the output current and the output voltage outputted from a cautery power source are controlled, the density of a current or a power applied to an organism tissue changes due to the area of a treatment tool to be in contact with the treatment portion of a patient and due to characteristics of the organism impedance. Therefore, it is difficult to perform incision or coagulation stanching. In addition, in an electric operation apparatus in which an increase in temperature at a treatment portion is detected by a temperature sensor formed at the top end of an electrode in a bipolar mode thereby to control the coagulation state, noise is mixed into a detection signal, due to the noise level of a high frequency current outputted from the electric operation apparatus itself, so that the detection accuracy is thereby influenced and makes it difficult to perform secure control.

As shown in FIG. 2, an electric operation apparatus 301 conventionally comprises a cautery power source 302 and a treatment tool 303. The cautery power source 302 comprises a power source circuit 322 which generates various voltages by means of an insulating transformer 321 from a power supplied by a commercial power source 304, a signal generator circuit 323 and a waveform shaping circuit 324 which generates signals basing waveform signals of high frequencies corresponding to various treatments such as incision, mixing or coagulation, from the power generated by the power source circuit 322, a high frequency power amplifier circuit 325 which subjects the signals generated by the waveform shaping circuit 324 to high-frequency amplification, a selection circuit 326 which switches the supply destination of the high frequency power amplified by the high frequency power amplifier circuit 325, between circuit of a bipolar mode and a mono-polar mode, and a CPU 327 connected with the selection circuit 326, the power source circuit 322, the signal generator circuit 323, the waveform shaping circuit 324, and the high frequency power amplifier circuit 325, thereby to control each of these circuits.

The selection circuit 326 is connected with a mono-polar output transformer 326a for a mono-polar mode and a bipolar output transformer 326b for a bipolar mode. Further, a mono-polar port 320a as an output end of the mono-polar output transformer 326a is connected with a treatment tool 331 corresponding to the mono-polar mode and with a patient electrode 332 for a returning current. A bipolar port 320b as an output end of the bipolar output transformer 326b is connected with a bipolar treatment tool 333 corresponding to the bipolar mode.

In addition, the CPU 327 is connected with a main panel 328 for selecting various waveforms and for setting various control values of circuits, and respective circuits are controlled by the CPU 327. Further, when an abnormal condition occurs, a treatment is taken in such a manner in which an operator is notified of the abnormal condition by an alarm circuit 329, while an output is stopped by the CPU 327.

As shown in FIG. 3, the characteristic of the high frequency power outputted from the cautery power source 302 changes such that the impedance characteristic of the output transformer such that this characteristic has a peak when the organism impedance is near 300Ω, and the impedance characteristic of the output transformer draws a damping curve from the boundary of the peak value, where the value outputted from an output transformer as an output circuit is set to 150 W or 300 W. Thus, the impedance characteristic of the peak value is changed, depending on the organism impedance, so that the cutting quality of the treatment tool and the stanching performance become unstable. Therefore, when an electric operation apparatus is used to perform a treatment, the output power and the output time with respect to a portion to be treated are set, depending on operator's perception and experiments over years, in view of conditions of a treatment portion observed with eyes.

In order to avoid this problem, Japanese Patent Application KOKOKU Publication No. 5-85177 shows an electric operation apparatus, as shown in FIG. 4, in which the high frequency output characteristic is smoothed to be flat with respect to the organic impedance.

Next, problems of the first prior art technique described above will be explained. In the case where the shapes of the connectors of counter plates are changed so that the type of counter can be distinguished, in order to determine the type of counter, the structure of an associated connecting portion must be complicated and this method therefore leads to an increase in costs. In addition, when the type of counter plate to be used is selected by a user the user may cause an operation error and this method is therefore also not desirable.

Further, problems of the second prior art technique described above will be explained. In accordance with developments in technical improvements in recent years, an electric knife apparatus is used over various fields such as an endoscopic treatment, a surgical operation, and the like. At present, an electric knife apparatus is indispensable in an hospital. Accordingly, in response to such demands, a so-called general purpose electric knife apparatus has been developed which responds to any aspects of techniques and is highly useful.

This electric knife apparatus has a high output power source which deals with a high frequency, and tends to allow a high-frequency current to leak into an unintended route. This high-frequency current becomes a factor which causes an unintended burn in an operator or a patient.

Meanwhile, in the case of the monitor method described in Japanese Patent Application KOKOKU Publication No. 61-32016, a high frequency leakage current can be detected, and besides, safety is ensured somehow since an output value is controlled in accordance with detection results.

However, in a system in which this monitor method is combined with a endoscope, an endoscope code system in which the endoscope body and a counter plate are kept at an equal potential is adopted, in order to collect a high frequency current which once has leaked into the endoscope body and thereby to ensure secure safety for an operator and a patient. In this case, a high frequency current which has once leaked into the endoscope body is collected by the electric knife body through an endoscope code, so that direct risks do not occur with respect to a patient or so. Even so, the monitor system may erroneously operate due to another current which does not pass through a high frequency treatment portion.

In particular, if the tissue resistance has a high impedance or if the load is released, a high frequency current component which flows through an endoscope code is greater than a high frequency current component which flows through a tissue. In this state, a high frequency current flows through a route passing through the endoscope code in an active line, while a current does not substantially or, possibly at all, return to the counter plate side. Then, the value of the ratio IP/IA of the current Ip returning to the counter plate side to a current IA flowing through the active line decreases. Therefore, the output is restricted or stopped regardless of that a dangerous condition does not occur to a patient or an operator. Further, in the case described above, a current flows through the endoscope code, and this current is not for performing a treatment. This means that a wasteful current continues flowing, and serves as a factor which degrades the treatment efficiency.

In addition, in the case of spray coagulation which is considered as particularly useful in a coagulation treatment in a surgical operation, a flow route for a high frequency current must be ensured even when an electrode and a tissue are not in contact with each other. Therefore, the output release voltage must be high enough to cause a breakdown in the air, and the output release voltage should be approximately 6000 to $8000V_{P-P}$. Particularly, in case of spray coagulation, there is a situation that a high frequency leakage current easily leaks into circumstances unintended through a floating capacity.

Further, once a breakdown has occurred between an electrode and a tissue and arc discharging has started, the circuit is brought into a condition in which the circuit is applied with a load, the output voltage decreases and most of the high frequency current flows toward the tissue. Therefore, the high frequency leakage current substantially reaches a negligible level. However, when the distance between the electrode and the tissue is increased to be larger than a certain distance, the arc discharging stops and the load is released, so that the output voltage increases and a situation appears in which a high frequency leakage current easily occurs.

Next, problems of the third prior art technique will be explained. In a conventional electric operation apparatus as described above, since whether out not a high frequency voltage and a high frequency signal are outputted in desired waveforms is not detected when a high frequency signal is actually outputted by an electric knife, a treatment is sometimes insufficient or excessive, e.g., human organisms are sometimes burnt too much or are not cut sufficiently in an operation, so that desired results cannot be achieved in the operation.

Finally, problems of the fourth prior art technique will be explained. In the high frequency output characteristic shown in Japanese Patent Application KOKOKU Publication No. 5-85177, the high frequency output characteristic of the output circuit is fixed and the vicinity of the maximum value indicated by a broken line of the high frequency output is removed and a high frequency output characteristic is obtained, the high frequency output characteristic does not damp due to changes in organism impedance, it is impossible to output the maximum output value set in the electric operation apparatus. Therefore, this apparatus is not suitable for a treatment which requires a high output. In addition, the high frequency output from a cautery power source is not controlled by detecting the organism impedance, but only a high frequency power of a predetermined output value is outputted. Therefore, the apparatus cannot respond to changes in organism impedance and differences in impedance of a treatment tool connected to a cautery power source. Hence, the output time of a high frequency power and the like must be set in view of perception and experiments of an operator.

SUMMARY OF THE INVENTION

The present invention has a first object of providing an electric operation apparatus which attains higher safety by securely determining the types of counter plates with ease and by driving a monitor circuit to operate, when a counter plate of a mono-polar type and a counter plate of a separate type are used.

In addition, the present invention has a second object of providing an electric operation apparatus which is applicable to an endoscopic treatment and a surgical operation, and which attains improved safety by ensuring a monitor function of securely detecting a high frequency leakage current even when the apparatus is used in a system utilizing an endoscope code system.

Further, the present invention has a third object of providing an electric operation apparatus which attains improved safety during an operation by monitoring a waveform generated by a waveform generator means, thereby to prevent an unexpected output due to malfunctions and erroneous operations of the waveform generator means.

In addition, the present invention has a fourth object of providing an electric operation apparatus which achieves higher safety by detecting information about or changes in a high frequency cautery power source device and organism tissues, thereby to control the high frequency power outputted from the high frequency cautery power source device to a treatment tool, in accordance with purposes of treatments.

In order to achieve the first object described above, the electric operation apparatus according to the present invention comprises: counter plate connection means for connecting a counter plate of a mono-polar type and a counter plate of a separate type; first monitor means connected to the counter plate connection means, for monitoring a condition of the counter plate of the mono-polar type; second monitor means connected to the counter plate connection means, for monitoring a condition of the counter plate of the separate type; and detection means for making the first and second monitor means operate on the basis of a predetermined operation procedure, thereby to detect attachment conditions of the counter plates of respective types connected to the counter plate connection means.

In order to achieve the second object described above, the electric operation apparatus which performs a high frequency treatment on an organism tissue by means of a high frequency current comprises: high frequency generator means for generating a predetermined high frequency; an active line connected to the high frequency generator means and including an active electrode; a counter plate line connected to the high frequency generator means and including a counter plate; an endoscope code line for connecting an endoscope body for guiding the active line, with the counter plate line, thereby to maintain both of the body and the line at an equal potential; first monitor means for monitoring a current flowing through the active line; second monitor means for monitoring a current flowing through the counter plate line; third monitor means for monitoring a current flowing through the endoscope code line; and determination means for performing comparison by combining monitor results obtained from the first, second, and third monitor means, and for determining a use condition of the electric operation apparatus on the basis of a comparison result obtained by the comparison.

In order to achieve the third object as described above, the electric operation apparatus comprises: waveform generator means for generating and outputting a high frequency signal waveform; monitor means for monitoring the high frequency signal waveform generated by the waveform generator means; and control means for controlling a high frequency signal output from the waveform generator means, in accordance with a monitor result obtained by the monitor means.

In order to achieve the fourth object, in the electric operation apparatus according to the present invention, a high frequency power is supplied from a high frequency power source device to a treatment tool for treating an organism tissue, to perform an operation, the high frequency power source device comprising: an output circuit for outputting a plurality of types of high frequency powers; monitor means for monitoring at least one of an output value of a high frequency power outputted from the output circuit and an output value of a change in an organism tissue; and control means for controlling the output circuit, thereby to selectively output the plurality of types of high frequency powers, on the basis of the output values monitored by the monitor means.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 10 is a view for explaining a basic structure of an electric operation apparatus according to a first modification of the second embodiment where the apparatus is combined with an endoscope code system;

FIG. 11 is a view for explaining a basic structure of an electric operation apparatus according to a second modification of the second embodiment where the apparatus is combined with an endoscope code system;

FIG. 14 is a flow chart of sub-processing in the electric operation apparatus according to the second modification of the second embodiment;

FIGS. 19A and 19B are flow charts of data processing in the electric operation apparatus according to the third modification of the second embodiment;

FIGS. 26A, 26B, and 26C are views showing output waveforms of a leading edge detection means and a monitor means when an output from a control means is a continuous wave;

FIGS. 27A, 27B, and 27C are views showing output waveforms of a leading edge detection means and a monitor means when an output from a control means is a burst wave;

FIGS. 28A, 28B, and 28C are views showing output waveforms of a leading edge detection means and a monitor means when an output from a control means is a mixture wave;

FIG. 29 is a view for explaining the structure of a main part of an electric operation apparatus according to a fourth embodiment of the present invention;

FIG. 30 is a view for explaining the output characteristic of an internal transformer provided in an output circuit;

FIG. 31 is a characteristic view of a high frequency output from the output circuit;

FIG. 32 is another characteristic view of a high frequency output from the output circuit;

FIG. 33 is further another characteristic view of a high frequency output from the output circuit;

FIG. 34 is a view showing a relationship between a treatment tool, a foot switch, and a CPU of an electric operation apparatus;

DETAILED DESCRIPTION OF THE PREFERRED EMBODIMENTS

Figure 5:
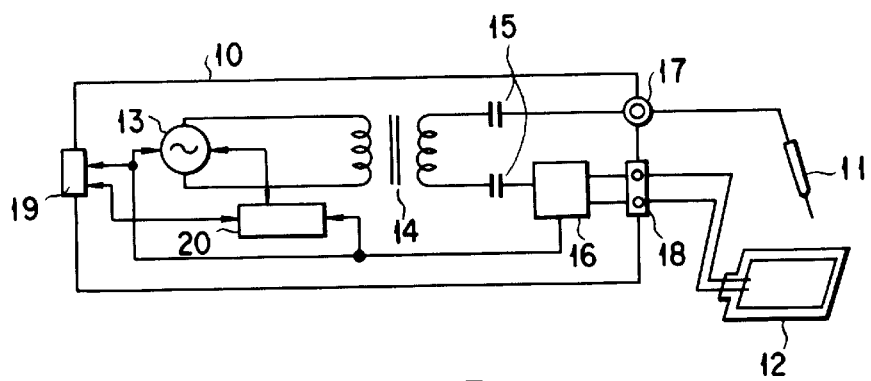
FIG. 5 is a view schematically showing a basic structure of an electric operation apparatus according to a first embodiment of the present invention.

In the following, the first embodiment of the present invention will be explained with reference to the drawings. FIG. 5 schematically shows a basic structure of an electric knife apparatus as an electric operation apparatus. In FIG. 5, the reference 10 denotes an electric knife body, the reference 11 denotes an electric knife hand piece, and the reference 12 denotes a counter plate. The electric knife body 10 is provided with a high frequency current generator circuit 13, an output transformer 14, low frequency cut capacitors 15, an output transformer 14 used for electric insulation, a low frequency cut capacitor 15, a counter plate monitor 16, an active connector 17, a counter plate connector 18, a display means 19, and a control means 20.

Further, the high frequency current generator circuit 13 generates a high frequency current for performing incision and coagulation functions, and the output transformer 14 performs insulation and voltage boosting. The output thereof is divided into an active side and a counter plate side, and the divided outputs are introduced to connectors 17 and 18 through low frequency cut capacitors 15 for preventing electric shocks. An active connector 17 is connected with a hand piece 11 which is operated by an operator. Incision and coagulation of a portion to be treated is carried out by applying a high frequency current outputted from the top end electrode of the hand piece 11, to the portion of a patient to be treated.

Meanwhile, the counter plate connector 18 is connected with a counter plate attached to a patient, and the high frequency current outputted from the hand piece 11 side is collected by a large area. Further, the condition of the counter plate 12 connected to the counter plate connector 18 is monitored by the counter plate monitor 16. As a result of this, if the condition of the counter plate 12 is abnormal an output inhibit signal is sent to the high frequency current generator circuit 13 or an abnormality signal is sent to the display means 19, thereby to perform abnormality display. These operations are controlled by the control means 20.

Figure 2:
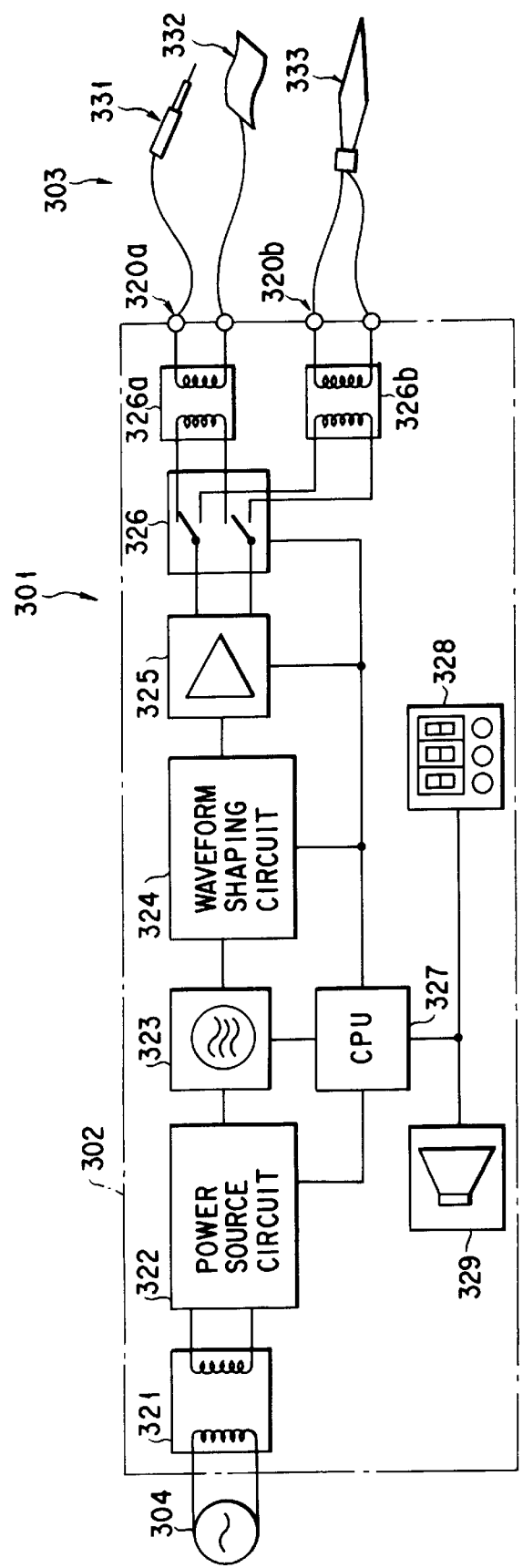
FIG. 2 is a view schematically explaining the structure of a conventional electric operation device.
Figure 3:
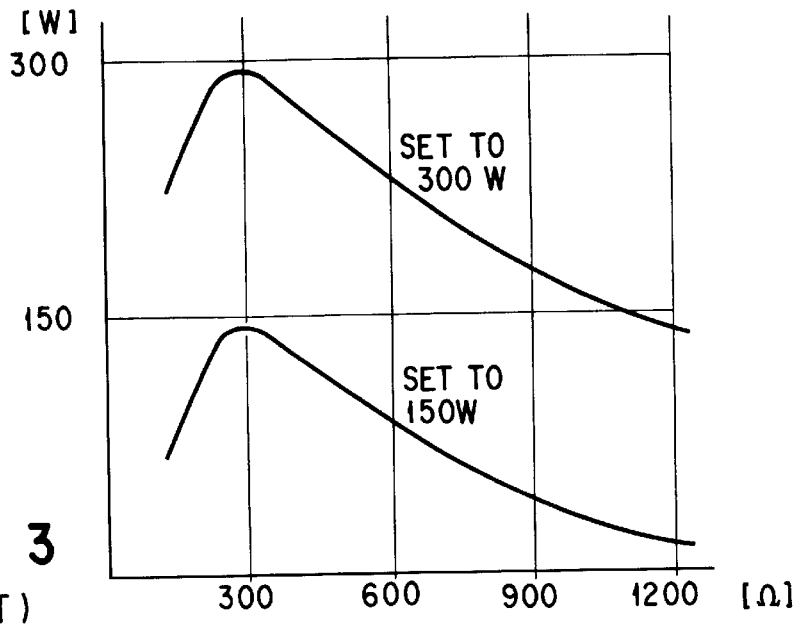
FIG. 3 is a view showing the relationship between an organism impedance and a high frequency output.
Figure 4:
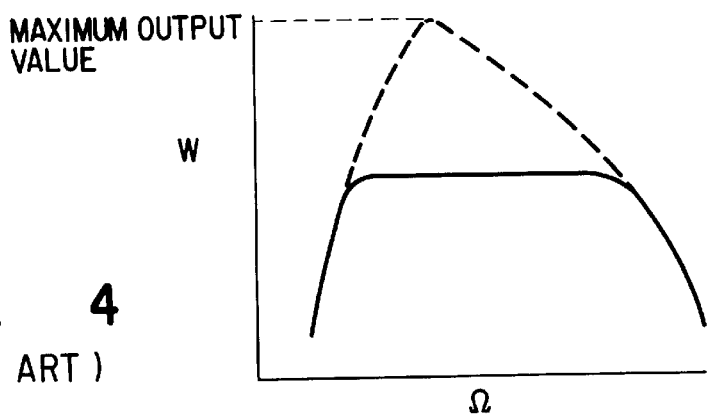
FIG. 4 is a view showing a flat high frequency output obtained by removing the vicinity of a maximum value.
Figure 6:
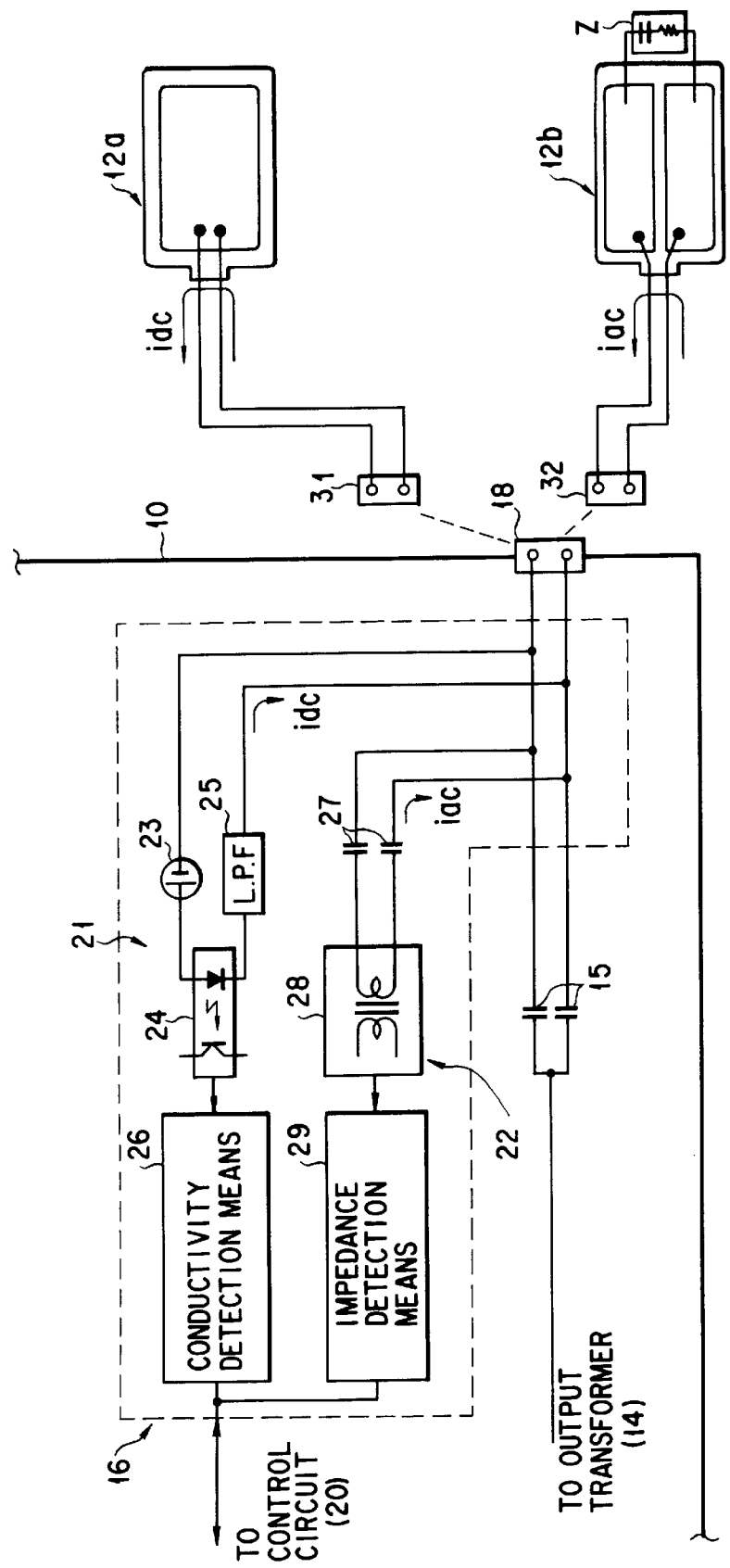
FIG. 6 is a view specifically showing a structure of an electric operation apparatus of a counter plate monitor of the same electric operation apparatus.

In the next, with reference to FIG. 6, the structure of the counter plate monitor 16 will be specifically indicated. Here, explanation will be omitted with respect to those portions which are the same as those of FIG. 2. Specifically, the monitor comprises the portion of a mono-polar counter plate monitor section 21 and the portion of a separate counter plate monitor section 22. At first, the mono-polar counter plate monitor section 21 comprises an independent power source 23, a photo-coupler 24, a low pass filter 25, and a conductivity detection means 26 for controlling the former components thereby to detect a conductivity. A terminal of a counter plate connector 18, the independent power source 23, a light-emitting diode of the photo-coupler 24, and the low pass filter 25 are connected in series thereby forming a closed loop circuit. Further, the output from the light receive element of the photo-coupler 24 is inputted into the conductivity detection means 26.

Meanwhile, the separate counter plate monitor section 22 comprises a direct current cut capacitor 27 which cuts a direct current, a pulse transformer 28, and an impedance detection means 29 for controlling former components thereby to detect the size of the impedance which has been subjected to the pulse transformer 28. Each of the mono-polar counter plate monitor section 21 and the separate counter plate monitor section 22 is connected to the counter plate connector 18.

Figure 1A:
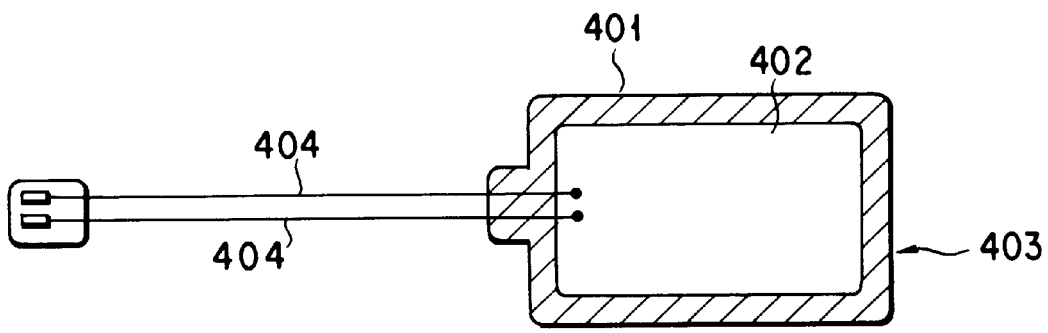
FIG. 1A is a view showing the structure of a counter plate of a mono-polar type.
Figure 1B:
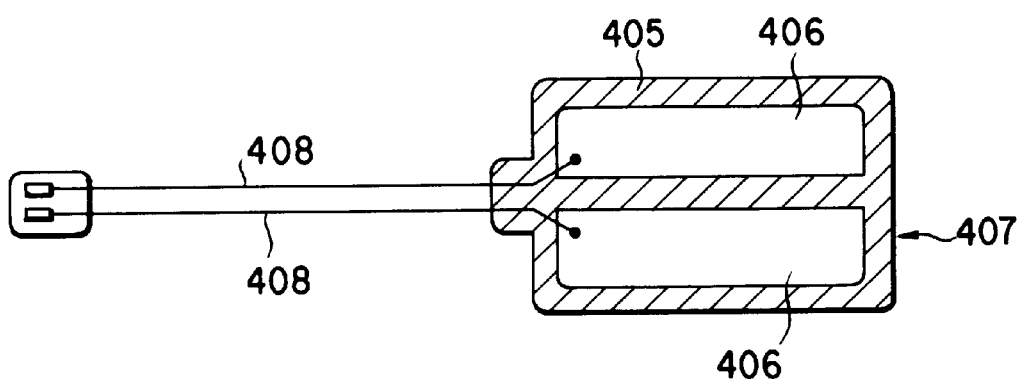
FIG. 1B is a view showing the structure of a counter plate of a separate type.

As a counter plate 12 to be connected to the counter plate connector 18, two types of counter plates are prepared, one being a mono-polar type counter plate 12a similar to the one explained with reference to FIG. 1A, and the other being a separate type counter plate 12b similar to the one explained with reference to FIG. 1B. In addition, the plug 31 of the mono-polar type counter plate 12a and the plug 32 of the separate type counter plate 12b are of an equal type and of a common type, and these plugs can be connected to one single counter plate connector 18 of the electric knife body 10.

When a counter plate 12a of a mono-polar type is used in this electric knife apparatus, the plug 31 is connected to the counter plate connector 18. Upon this connection, the independent power source 23 generates a direct current i dc, which passes through a low pass filter 25 and returns through a code of the counter plate 12a, thereby forming a loop. Therefore, a photo-coupler 24 is operated and transfers the signal to the conductivity detection means. The conductivity detection means 26 determines that the counter plate 12a of a mono-polar type is correctly connected or that no code is broken. The determination result is transmitted to the control circuit 20, and desired operation is performed.

Meanwhile, when a counter plate 12b of a separate type is used, the plug 32 thereof is connected to the counter plate connector 18. Upon this connection, the impedance detection means 29 is operated and a slight alternating current power source i ac is generated from the second side of the pulse transformer 28. This current passes through a direct current cut capacitor 27 and passes through a code of the counter plate 12b, thereby forming a loop including an impedance Z obtained when the separate type counter plate 12b is attached to a patient. In this manner, a signal expressing the size of the attached impedance Z appears in the first side of the pulse transformer 28, and is transmitted to the impedance detection means 29. As a result of this, it is determined that the counter plate 12b of a separate type has been correctly attached to a patient or that no code is broken. The determination result is transmitted to the control circuit 20, so that a desired operation is performed. Here, the low pass filter 25 and the direct current cut capacitor 27 execute a function of preventing interference between their own detection currents (i ac and i dc).

Figure 7:
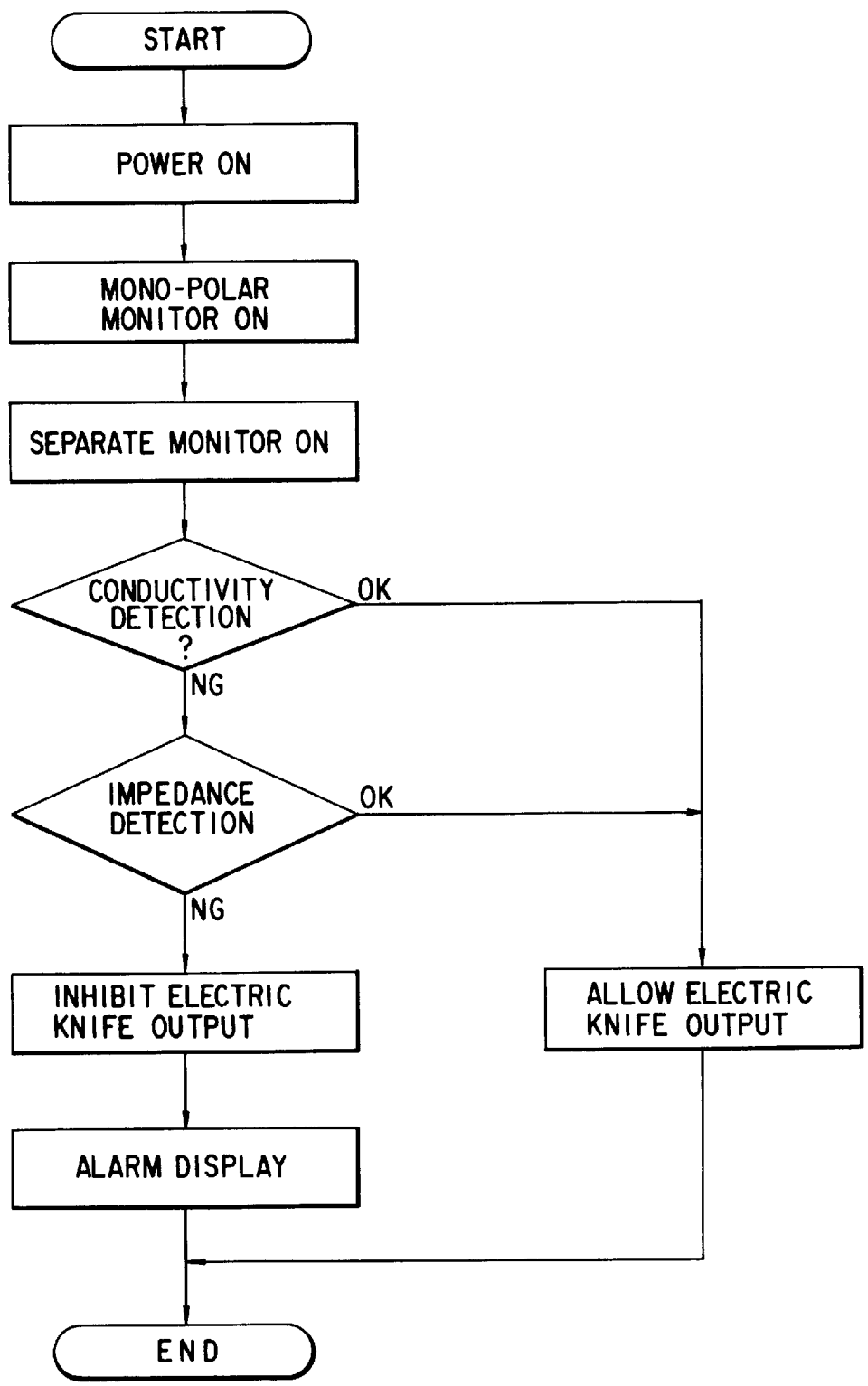
FIG. 7 is a flow chart showing a procedure of an example in which the counter plate is monitored.

In the next, a first example of monitoring a counter plate 12 in the above structure will be explained in accordance with the flow shown in FIG. 7. When the power source is turned on by a switch or the like not shown, the counter plate monitor section 21 of a mono-polar type and the counter plate monitor section 22 of a separate type are started. As for a monitor section 21 of a mono-polar type, if the result of the conductivity detection means 26 is "OK", the output of electric knife is allowed. If the result of the conductivity detection means 26 is "NG", the output of the electric knife is allowed when the result of the impedance detection means 29 is "OK", as for the monitor of a separate type. If the result of the impedance detection means 29 is "NG", it is determined that the counter plate 12 is not positioned correctly any more, and the output of the electric knife is inhibited, and alarm display or the like is performed. In this method, monitoring of respective counter plates 12a and 12b can continue.

Figure 8:
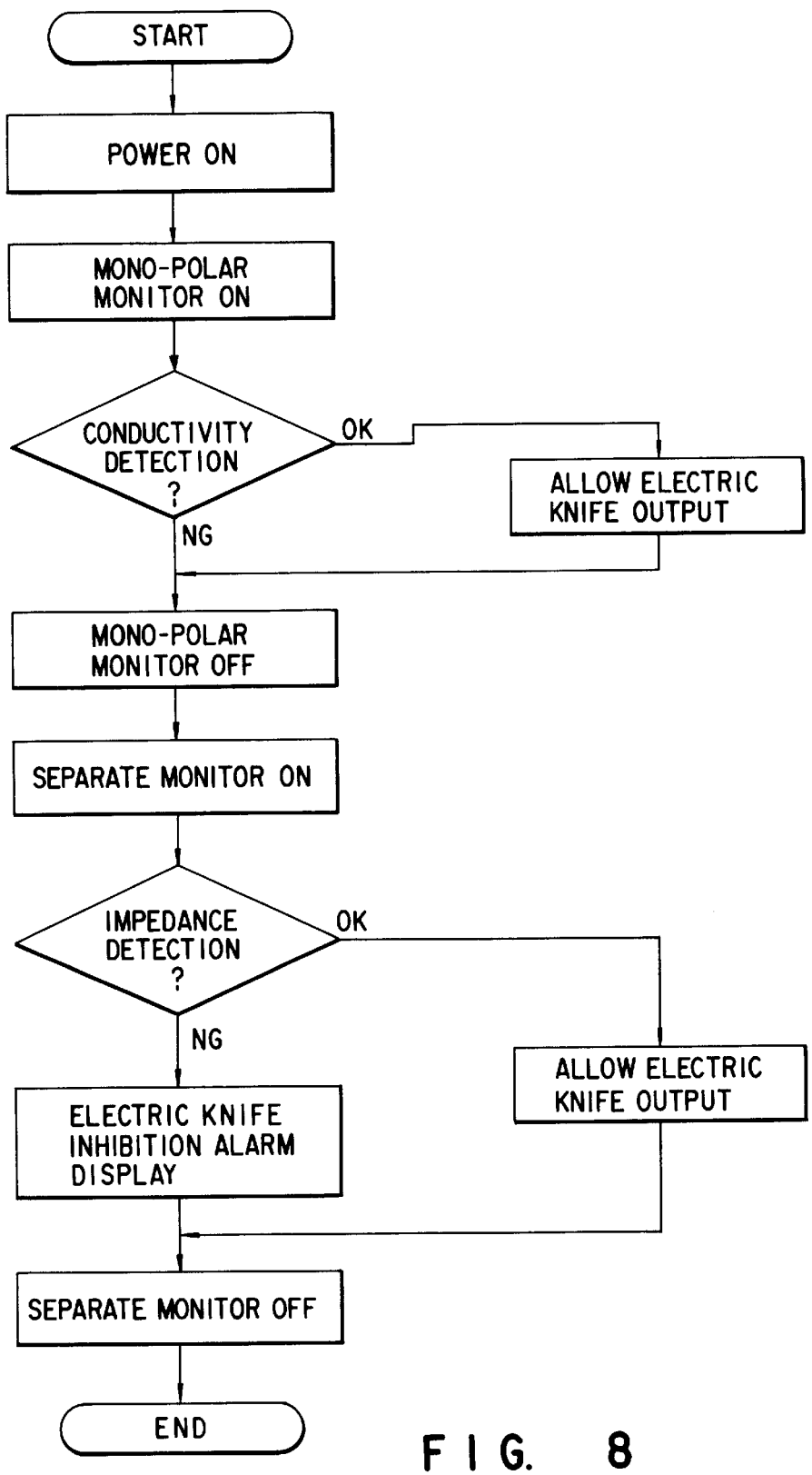
FIG. 8 is a flow chart showing a procedure of another example in which the counter plate is monitored.

In the next, a second example of monitoring the counter plates 12 in the above structure will be explained in accordance with the flow shown in FIG. 8. Once the power source is turned on, the counter plate monitor section 21 of the mono-polar type is started. If the result of the conductivity detection means 26 as a mono-polar type monitor is "OK", the output of the electric knife is allowed, and the operation of the counter plate monitor section 21 of the mono-polar type is stopped, including a case in which the result is "NG".

Thereafter, the counter plate monitor 22 of the separate type is started. If the result of the impedance detection means 29 as the separate type monitor, is "OK", the output of the electric knife is allowed. Further, in case of "NG", it is determined that the counter plates 12 are not positioned correctly any more. Then, the output of the electric knife is inhibited and alarm display is performed, while the operation of counter plate monitor 22 of the separate type is stopped. In this method, monitor sections 21 and 22 of their own are time-divisionally operated, so that interference therebetween can be eliminated.

Note that the present invention is not limited to the procedures as described above, it is possible to monitor the condition of the counter plate 12, by making respective monitors function upon necessary.

According to the first embodiment as described above, it is not necessary to provide any particular means for determining the types of counter plates, but monitoring can be performed in accordance with the types of the plates. Therefore, it is possible to obtain an advantage in that the condition of the counter plates can be securely be determined with ease and the safety of the apparatus is much more improved.

Figure 9:
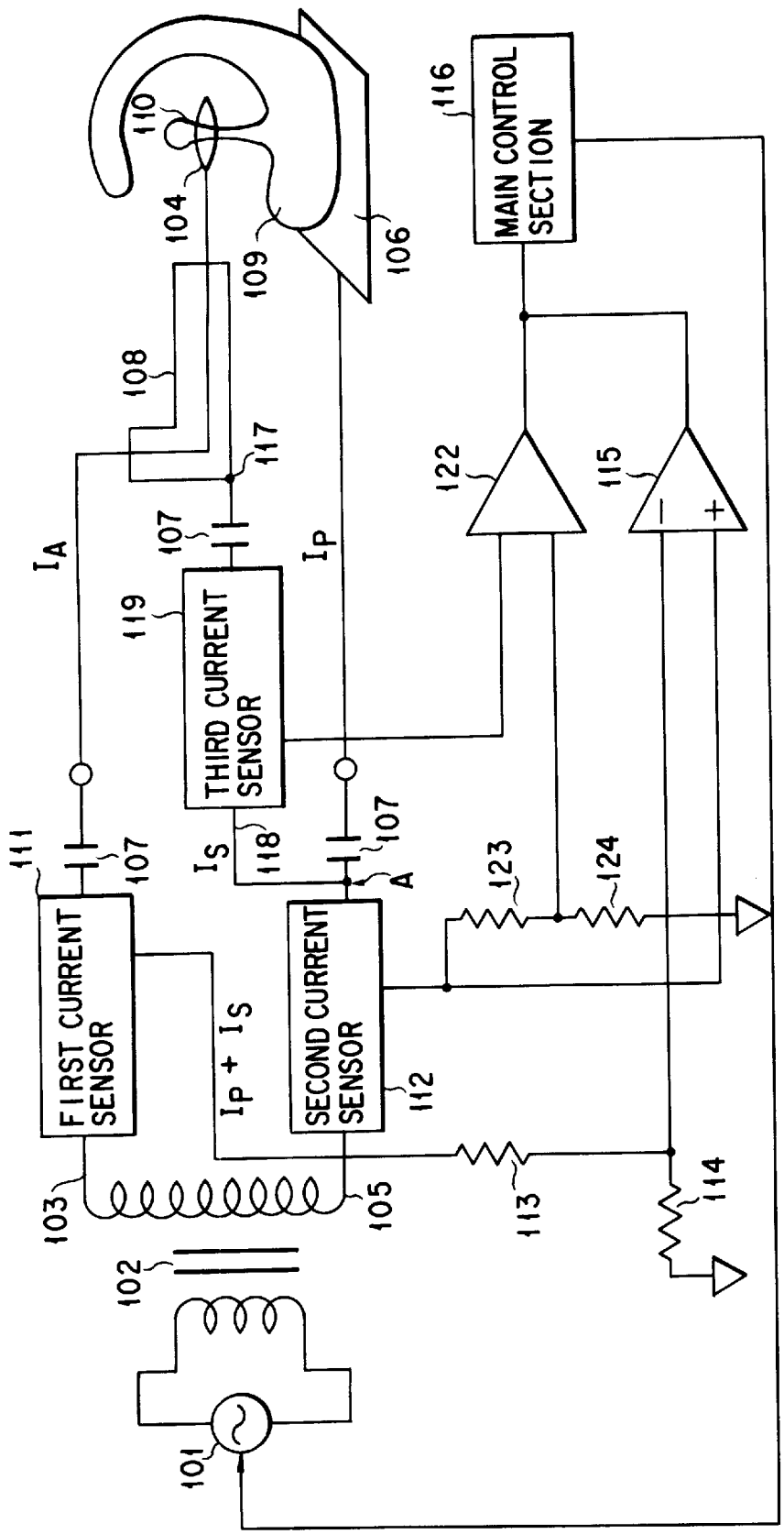
FIG. 9 is a view for explaining a basic circuit structure of an electric operation apparatus according to a second embodiment where the apparatus is combined with an endoscope code system.

In the next, a second embodiment of the present invention will be explained, FIG. 9 shows a basic circuit configuration of an electric operation apparatus in combination with an endoscope code system (which will be referred to as an electric knife apparatus). This electric knife apparatus, for example, comprises a high frequency generator source (or high frequency generator means) 101 having an LC resonance circuit. An end of a secondary coil of an output transformer 102 in the LC resonance circuit of the high frequency oscillator source 101 is connected with an active line 103, and the top end of the active line 103 is connected with an active (treatment) electrode 104. Another end of the secondary coil of the output transformer 102 is connected with a counter plate line 105, and the top end of this counter plate line 105 is connected with a counter plate 106. The active line 103 is introduced into a body cavity of a patient 109 through a channel of the endoscope 108.

The active line 103 is provided with a first current sensor (or first monitor means) 111, and a second current sensor (or second monitor means) 112 is provided in the middle of the counter plate line 105. Further, the first current sensor 111 detects a current flowing through the active line 103, and the second current sensor 112 detects a current flowing through the counter plate line 105. Each of the current sensors 111 and 112 outputs a detected current value in form of a direct current signal.

A detection signal which is detected by the first current sensor 111 and flows through the active line 103 is voltage-divided by through the resistors 113 and 114, and a voltage-divided signal is inputted into an inverted input terminal of the first comparator 115. In addition, a detection signal of a current which is detected by the second current sensor 112 and flows through the counter plate line 105 is inputted into a non-inverted input terminal of the first comparator. An output of the first comparator 115 is supplied to a main control section 116.

Here, a second current sensor 112 provided on the counter plate line 105 is positioned a rear stage of the position of a connection point A between an endoscope code 117 and a counter plate line, i.e., in the side close to the high frequency oscillator source.

In addition, the line from the body of the endoscope 108 to the endoscope code 117 is provided with a third current sensor (or third monitor means) 119. This third current sensor 119 detects a current flowing through the line 118, and converts this current into a direct current signal, which is outputted. An output signal of the third current sensor 119 is inputted an input terminal of the second comparator 122. In addition, another input terminal of the second comparator 122 is inputted with a detection signal of the second current sensor 112 voltage-divided by the resistors 123 and 124. The output of this second comparator 122 is supplied to the main control section 116. The main control section 116 controls the operation of the high frequency oscillator source 101, in response to outputs of the comparators 115 and 122, as will be described later.

A capacitor 107 is inserted in the middle of the each line 103, 105, and 118, in order to prevent electric shocks for a patient, thereby forming a low frequency elimination means.

In the next, the function of the electric knife apparatus will be specifically explained. When an electric knife apparatus is used, a treatment mode is selected by an operation panel not shown, as a part of preparation procedures. For example, a spray coagulation mode is selected among an incision mode, a coagulation mode, a spray coagulation mode and the likes. In addition, an active electrode 104 of a high frequency treatment tool is guided into an affected part in the body cavity.

Then, when the electric knife apparatus is operated by operating an output switch not shown, the high frequency oscillator source 101 oscillates and generates a high frequency power. This high frequency power is voltage-boosted by the output transformer 102, and is supplied to an affected tissue 110 of a patient 109 from the active electrode 104 through the active line 103. In this state, a functional current which creates a treatment effect passes through an tissue 110 through a counter plate 106 and a counter plate line 105, and is finally collected by another end of the output transformer 102 of the electric knife body.

Here, the current flowing through the active line 103 and the current flowing through the counter plate line 105 are respectively detected by associated current sensors 111 and 112, and converted into direct current signals. These signals are compared with each other in the first comparator 115, thereby to make a determination as to an abnormal condition.

The determination as to an abnormal condition is performed in the following manner. Specifically, a detection current of the current flowing through the counter plate line 105 is inputted into the non-inverted input terminal of the first comparator 115, while a detection signal of the current flowing through the active line 103 is inputted into the inverted input terminal thereof, in form of a signal voltage-divided by the resistors 113 and 114. The first comparator 115 obtains a ratio IP/IA of the current IP fed back to the counter plate line 105 to the current IA flowing through the active line 103, and an output as the result is supplied to the main control section 116. The main control section 116 makes a determination as to an abnormality, from results thus supplied. Further, adjustment of the threshold level for determining the abnormality is made, depending on the ratio of resistance values of the resistors 113 and 114, and therefore, adjustments can be easily performed. For example, in order to obtain a determination of an abnormal condition when the ratio IP/IA is 50% or less, the values of the resistors 113 and 114 are set to an equal value. In response to results thus compared, the main control section 116 makes the high frequency oscillator source 101 disabled in an abnormal condition, and simultaneously issues an alarm.

Meanwhile, since the second current sensor 112 provided on the counter plate line 105 is positioned in the rear stage side of a connection point between an endoscope code 117 and a counter plate line 118, i.e., in the side close to the high frequency oscillation source, a current detected by the second current sensor 112 is obtained as a sum of the current (IP) flowing through the counter plate line 105 and the current (IS) flowing through the endoscope code 117. Then, for example, in case where the output end is opened, or in case where the impedance of a tissue 110 is increased to be high, there is a tendency that the current which passes through the tissue 110 and is fed back to the counter plate line 105 is decreased while the current IS which passes from the body of the endoscope 108 and through the endoscope code 117 is increased. However, the current detected by the second current sensor 112 provided in the side close to the counter plate line 105 is a sum of the current IP and the current IS, and the value of this sum is of a level substantially equal to the current IA flowing through the active line 103. Therefore, the ratio IP/IA of currents, more strictly, (IP+IS)/IA is not decreased, so that determination of an abnormal condition is not made.

However, in this state, the current flowing through the body of the endoscope 108 is collected by the electric knife body through the endoscope code 117, and therefore, burns are not caused at an ocular portion of the endoscope 108, for an operator. In addition, the body of the endoscope 108 is in contact with a patient by a sufficient area, currents are sufficiently diffused so that the current density is sufficiently decreased and there is no possibility that burns or the like may occur at the contact portion with the endoscope 108. Thus, a safe condition is maintained. Therefore, there are no problems when a determination of an abnormal condition is issued.

Note that a high frequency leakage current can be detected by the method as described above, when surgical techniques are taken.

Meanwhile, when a short-circuit occurs between the active electrode 104 connected to the active line 103 and a metal portion of the body of the endoscope 108, a large amount of current flows through the metal portion of the body of the endoscope 108. However, with only the method described above, since the short-circuit current flows in a route from the active line 103 through the endoscope code 117 and is fed back to the body, the signal levels detected by the first current sensor and the second current sensor 112 a an equal level, so that the monitor is not determined as being abnormal. However, in this state, a large amount of current flows through the body of the endoscope 108, and therefore, there is not only a possibility that burns occurs in an operator, but also a possibility that degradation in insulation of the body of the endoscope 108 may occur and a heat may be generated.

Therefore, according to this embodiment, not only the ratio of current values described above is compared and calculated, but also a third current sensor 119 is provided to monitor the ratio (IP/IS) of the current (IS) flowing through the endoscope code 117 to the current (IP) flowing through the counter plate line 105, by means of a second comparator 122, and the output thereof is supplied to the main control section 116, thereby to make a determination as to an abnormality. The method of detection thus performed is similar to that used for monitoring the ratio (IP/IA) described above, and the threshold level used for determining abnormality is decided by the ratio of resistances of the resistors 123 and 124.

In the following, the first modification of the second embodiment described above will be explained. FIG. 10 shows a basic circuit configuration of an electric knife apparatus where this electric knife apparatus is combined with an endoscope code system. As for an output of the electric knife, a user decides a desired waveform mode and an output setting value by means of a setting panel 131, and information thus set is supplied to the main control circuit section 132. The main control circuit section 132 supplies a wave selection signal and power data according to the information, to a waveform generator section 133 and a variable power source 134, respectively. In the waveform generator section 133, a signal having a waveform according to the waveform selection signal from the main control circuit section 132, and supplies this signal to the power amplifier 135. In addition, in the variable power source 134, a power is generated in accordance with the power data from the main control circuit section 132, likewise. The power amplifier 135 which is supplied with a waveform signal generated by the waveform generator section 133 for supplying the power to the power amplifier and which is also supplied with a power generated by the variable power source 134 constitutes a high frequency generator means for generating a high frequency power.

The high frequency power generated by the power amplifier 135 is transmitted by the output transformer 136, and is supplied to a tissue 138 through the active line 137 connected to an end of the second coil of the output transformer 136, and this power is collected by the electric knife body 136 through the counter plate line 139 connected to another end of the second coil of the output transformer 136. The top end of the counter plate line 139 is provided with a counter plate 140.

In case where a technique of adopting an endoscope code system is used, the active line 137 is inserted into a channel of the endoscope body 141, and the endoscope body 141 is connected with the endoscope code 142.

Like in the second embodiment as described above, the active line 137 is provided with a first current sensor 143, the counter plate line 139 is provided with a second current sensor 144, and the line of the endoscope code 142 is provided with a third current sensor 145. Here, the main control section 132 may control the high frequency output, depending on the values of currents respectively flowing through the lines compared by means of comparators 115 and 122. However, in particular, a means for controlling the output of the power amplifier 135 described below has already been incorporated in the first modification.

Specifically, a comparator 146 is provided to compare the level of an output signal of a first current sensor 143 which detects a current flowing through the active line 137 and which converts this current into a direct current signal detected, with the level of an output signal of a third current sensor 145 which detects a current flowing through the line of the endoscope code 142 and converts this current into a direct current signal. The difference between the current levels flowing through the lines is detected and the waveform generator 133 or the variable power source 134 is controlled in accordance with the level difference, thereby to change the output of the power amplifier 135, i.e., the output of the high frequency generator means.

Here, assuming that, for example, a tissue 138 has a high impedance due to the cautery process or the load of a tissue 138 is released, when an electric knife apparatus is used, the current flowing from the active line 137 toward the tissue 138 is decreased while the current flowing through the endoscope body 141 is increased due to a floating capacity existing between the endoscope body 141 and an electrode inserted in the endoscope body 141. In this state, the current flowing through the endoscope body 141 is not a functional current for performing a treatment on the tissue 138, but is an invalid current which is merely collected by the electric knife body through the endoscope code 142. This invalid signal is only converted into a heat by a metal blade provided in the endoscope body 141 and by the output transformer 136 inside the body. This means that a very wasteful current is generated.

Therefore, an output signal of the first current sensor 143 for detecting a current flowing though the active line 137 and for converting this current into a direct current signal is compared at the comparator 146 with an output signal of a third current sensor 145 for detecting a current flowing through the line of the endoscope code 142 and for converting this current into a direct current signal. If both of the detection signals are of an equal level, it is determined that a functional current used for actually treating a tissue 138 is decreased and an invalid signal flowing through the endoscope code 142 is increased, and the output of the variable power source 134 is restricted, depending on the condition of an output signal of the comparator 146, or a signal is supplied to a waveform generator section 133 to suppress the output waveform thereof, so that the output value of the power amplifier 135 is decreased. In this manner, a wasteful power is not generated, and as a result, an effective treatment can be performed.

According to this method, with respect to an invalid current which inevitably leads into an endoscope body in a technique using an endoscope system, the output can be adjusted by monitoring the current flowing in the output circuit, so that an operation can be achieved at a high efficiency with less wasteful losses.

In the following, a second modification of the second embodiment will be explained. As shown in FIG. 11, the basic structure of this modification is the same as that of the second embodiment described above. However, the second modification includes a function of digital detection in comparison with the second embodiment in which a high frequency leakage current is detected by an analogue measure.

In FIG. 11, an active line 103, a counter plate line 105, and an endoscope code line 118 are respectively provided with current sensors 111, 112, and 119. Currents flowing through these lines are respectively detected by the current sensors 111, 112, and 119, and are converted into direct current signals. Analogue signals outputted from the current sensors 111, 112, and 119 are respectively taken into corresponding A/D converter means 151, 152, and 153, where the signals are converted into digital data. The data of these converted digital signals are sent to the main control section 116, and are taken in by the CPU (not shown) provided in the main control section 116. Further, calculations and comparisons are performed in the CPU, thereby to make a determination as to an abnormal condition. This data processing flow will be explained below.

The flows shown in FIGS. 12 to 16 are distinguished from each other depending on the difference in techniques or methods, and determination as to which one of the processing flows should be carried out is made by detecting presence or absence of a connection state of the endoscope code.

Figure 12:
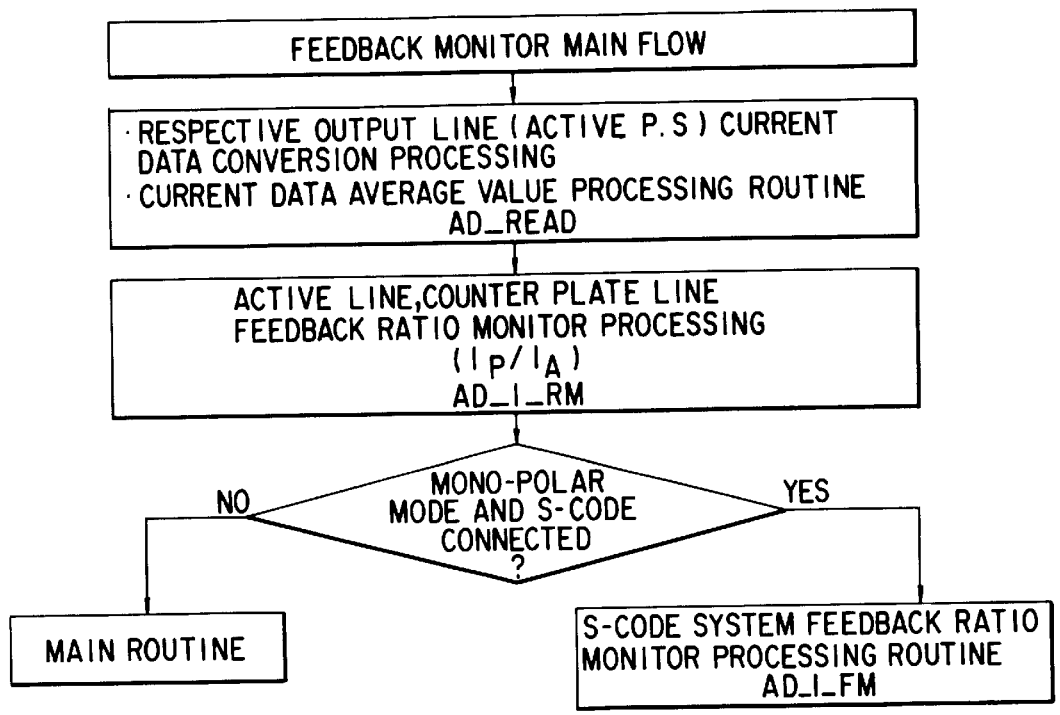
FIG. 12 is a flow chart of data processing in the electric operation apparatus according to the second modification of the second embodiment.
Figure 13:
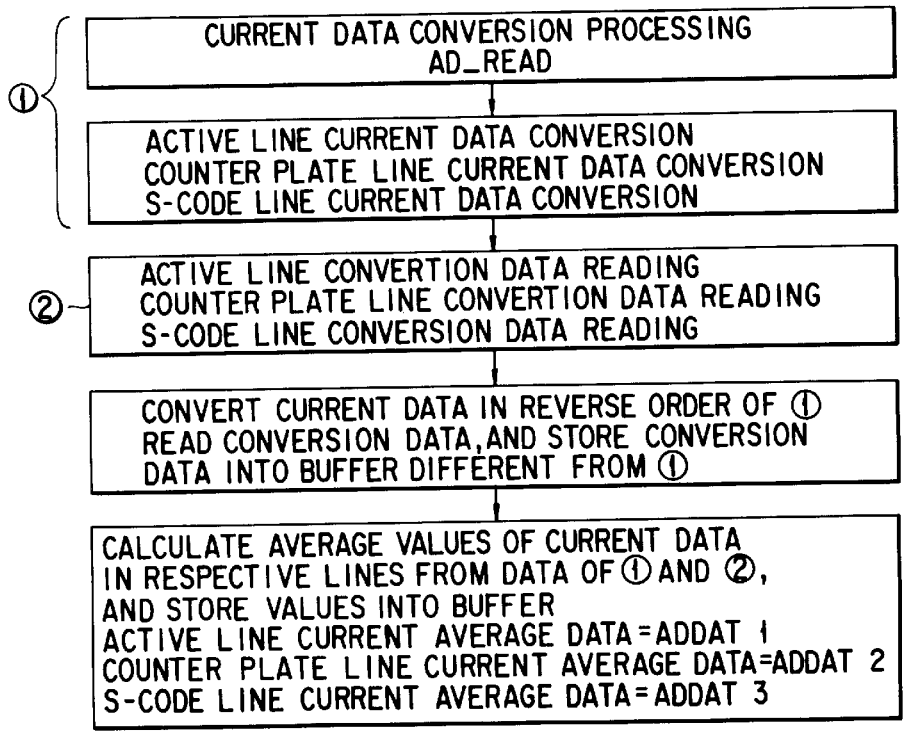
FIG. 13 is a flow chart of main processing in the electric operation apparatus according to the second modification of the second embodiment.
Figure 15:
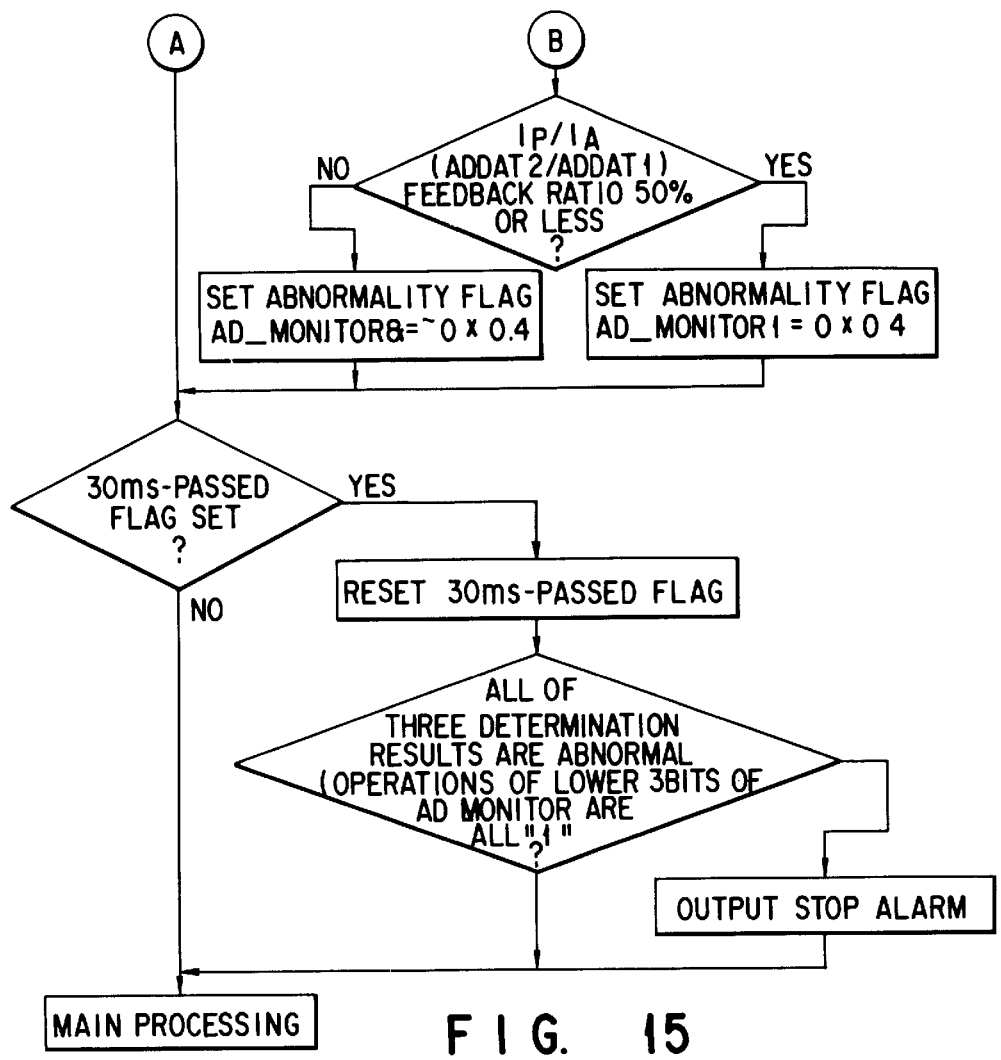
FIG. 15 is a flow chart of sub-processing following the former flow chart in the electric operation apparatus according to the second modification of the second embodiment.
Figure 16:
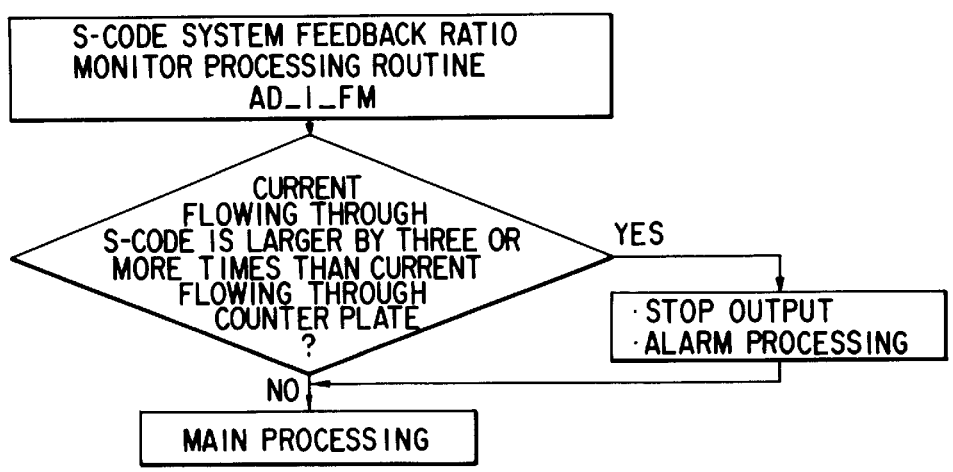
FIG. 16 is a flow chart of other sub-processing in the electric operation apparatus according to the second modification of the second embodiment.

FIG. 12 is a main flow of a current feedback ratio monitor including a case using an endoscope code system, and FIG. 13 is a flow showing current data conversion, reading, and calculation processing. FIG. 14 and FIG. 15 are flows of a feedback ratio monitor of IP/IA. FIG. 16 is a flow of a feedback ratio monitor of IS/IP.

When current feedback ratio monitoring is performed when using an endoscope system, current data conversion, reading, and calculation processing are performed in accordance with the flow of FIG. 13. Specifically, calculation parameter definition is performed to convert data of currents respectively flowing the active line 103, counter plate line (or P line) 105, and the endoscope code line (S line) 118, and the converted data are respectively read and stored into a memory.

In the next, converted data is read into a buffer again, in a reverse order of the order in which the first data reading is performed. This is because it is very difficult to perform data conversion and reading by an A/D conversion means at one same timing under restrictions of hardwares, although detection would rather be performed with a higher accuracy by converting currents flowing at one same instance on time series when detection is to be performed. Therefore, in order to attain accuracy close to the detection accuracy obtained in the above-mentioned method, data conversion and reading are performed twice while changing the order of procedures.

Average values of these data are respectively stored as final data into an active line current average value storage buffer (ADDAT1), a P line current average value data storage buffer (ADDAT2), and an S line current average value data storage buffer (ADDAT3) corresponding to those data. Specifically, converted data corresponding to currents flowing through respective lines are stored in different areas on the memory.

On the basis of these data, various monitor processing can be performed. For example, when the current IA flowing through the active line 103 is 250 mA or more, a determination of an abnormal output is made, and processing for issuing an alarm and stopping the output is performed. In particular, feedback ratio monitor processing of IP/IA and feedback ratio monitor processing are performed.

The feedback ratio monitor processing of IP/IA is performed by the flow shown in FIGS. 14 and 15. At first, current data IA and IP are read out and the ratio of IP/IA is calculated, for every 10 ms as the timer counts up. For every calculation, it is determined as abnormal if the ratio is equal to or lower than a predetermined value, e.g., 50%, and in this case, an abnormality flag is set while this abnormality flag is reset in the other cases. In addition, when 30 ms have passed, the timer is clear and a 30 ms-passed flag is reset.

IN the next, whether or not a 30 ms-passed flag is set is determined. If this flag is set and if all of the determination results of calculations are abnormal, an alarm is issued and an output is stopped. Thus, the ratio of IP/IA is calculated and determination of thereof are performed for a plurality of times, and on the basis of the calculations and determinations, a final determination is made. Therefore, erroneous detection due to noise or the like is prevented and the detection accuracy is improved.

In addition, in the case of using an endoscope code system, at the same time when a ratio of a current value IP flowing through the counter plate line 105 to the current value IA flowing through the counter plate line 103 is calculated, a ratio of a current value IS flowing through the endoscope code line 118 to a current value IP flowing through the counter plate line 105 is performed (see the flow of FIG. 16). Specifically, when the feedback ratio of IS/IP is equal to or more than a constant value, e.g., when the current value 1S is as three or more times greater than the current value IP flowing through the counter plate line 105, it is determined that there occurs an abnormal condition which may be caused when this current is used in an endoscope code system, i.e., that an alternating current is generated or that a short circuit occurs between an electrode of a high frequency treatment tool and a metal portion of the endoscope body, and this abnormal condition is securely detected. Further, if the output is abnormal, an alarm means such as an LED or the like is operated and the output is stopped.

Note that the above described feed back ratio monitor processing flow concerning the ratio IP/IA is effective when an endoscope code system is not used, i.e., when the apparatus is used in a surgical operation. This case is characterized in that the endoscope code 117 is not connected, and therefore, only the ratio of the current value of the current flowing through the counter plate line 105 to the current value of the current flowing through the active line 103 is detected. As a result of this, in case where an operation is performed in the setting where the output is relatively high, a high frequency leakage current can be securely detected (or a partial flow can be detected).

In addition, if the apparatus is arranges so as to incorporate both of the high frequency leakage current detection using an analogue method shown in the second embodiment and the other high frequency leakage current using a digital method according to the second modification, it is possible to ensure much more safety and security. In this case, the processing flow will be modified, more or less, but explanation of such a modified processing flow will be omitted.

Further, with respect to an output automatic control function as has been shown in the second embodiment, digital processing shown in the second modification can be performed. Further, if the accuracy must be increased, the processing can be performed with incorporating both of the different methods.

Figure 17:
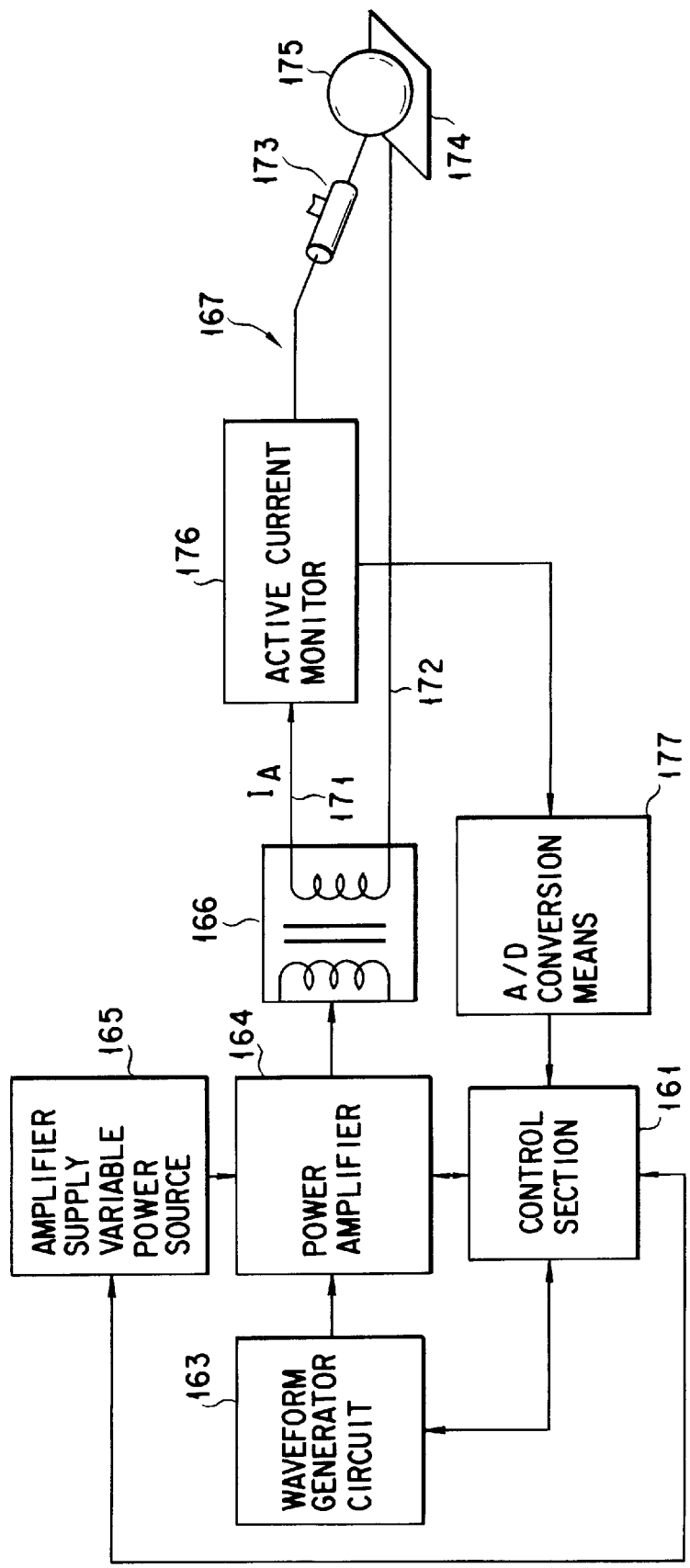
FIG. 17 is a view for explaining a basic circuit structure of an electric operation apparatus in which the apparatus is combined with an endoscope code system according to a third modification of the second embodiment.

In the following, a third modification of the second embodiment will be explained with reference to FIG. 17. In this figure, the reference 161 denotes a control section, and this control section 161 controls the entire electric knife, including waveform mode selection designated by an operation state of an output switch not shown and by an operation panel, supply of a control voltage corresponding to a high frequency output setting value to be supplied to a variable power source 165, supply of a waveforms selection signal selected, and the like. The following explanation will be made, assuming that the spray coagulation mode is selected.

Once the spray coagulation mode is selected, the control section 161 sends a waveform selection signal to a waveform generator circuit 163, in order to generate a waveform of the spray coagulation mode. The waveform generated by the waveform generator circuit 163 is inputted into, for example, a gate of a power MOSFET of a switching means constituting a power amplifier stage of the power amplifier 164. Meanwhile, the control section 161 sends not only a waveform signal, but also a control voltage according to the set value of the signal, to a variable power source 165 which decides the high frequency output. The variable power source 165 generates a power according to the control voltage, and supplies it to the power amplifier 164. The power amplifier 164 receives these wave form and power, and generates a high frequency by creating a resonance through an LC parallel circuit. The high frequency thus obtained is transmitted to an output circuit 167 will be describtransfer by an output transformer 166.

An end of the output transformer 166 is connected with an active line 171, while another end thereof is connected with a counter plate line 172. The top end of the active line 171 is connected with an active electrode 173, while the top of the counter plate line 172 is connected with a counter plate 174. Further, the output circuit 167 described above is constituted by the active line 171, the active electrode 173, a tissue 175, the counter plate 174, and the counter plate line 172.

In addition, on the active line 171 of the output circuit 167, an active current monitor 176 for detecting a current IA flowing through this line 171 is provided, and the active current monitor 176 detects the current IA and converts it into a direct current signal. An analogue signal of the active current monitor 176 is converted into digital data by an A/D converter means 177. This digital data is taken in by the control section 161 and is subjected to processing which will be explained below.

Here, for example, when the output circuit 167 is opened, i.e., when the electrode 173 and the organism tissue 175 are out of operational distance range, arc discharging does not take place therebetween, and the output releasing voltage is very high, so that a high frequency leakage current is easily generated. In this case, i.e., when arc discharging does not take place, the output circuit 167 is in a condition of open circuit, and a current does not flow through the output circuit 167.

Meanwhile, when the distance between the electrode 173 and the organism tissue 175 is within an operational distance range, arc discharging takes place and a current flows through the output circuit 167. Specifically, in this state, the output circuit 167 is a closed circuit. When arc discharging takes place at the output end, the state of the arc discharging can be detected, depending on the state of the current IA flowing through the output circuit 167. Specifically, an active current monitor (or current sensor) 176 provided in the active line 171 as a component of the output circuit 167 detects the current IA flowing through the output circuit 167, and converts this current into a direct current signal. Further, this signal is converted into digital data by an A/D converter means 177, and this digital data is taken in by the control section 161 where this data is processed as follows.

Figure 18:
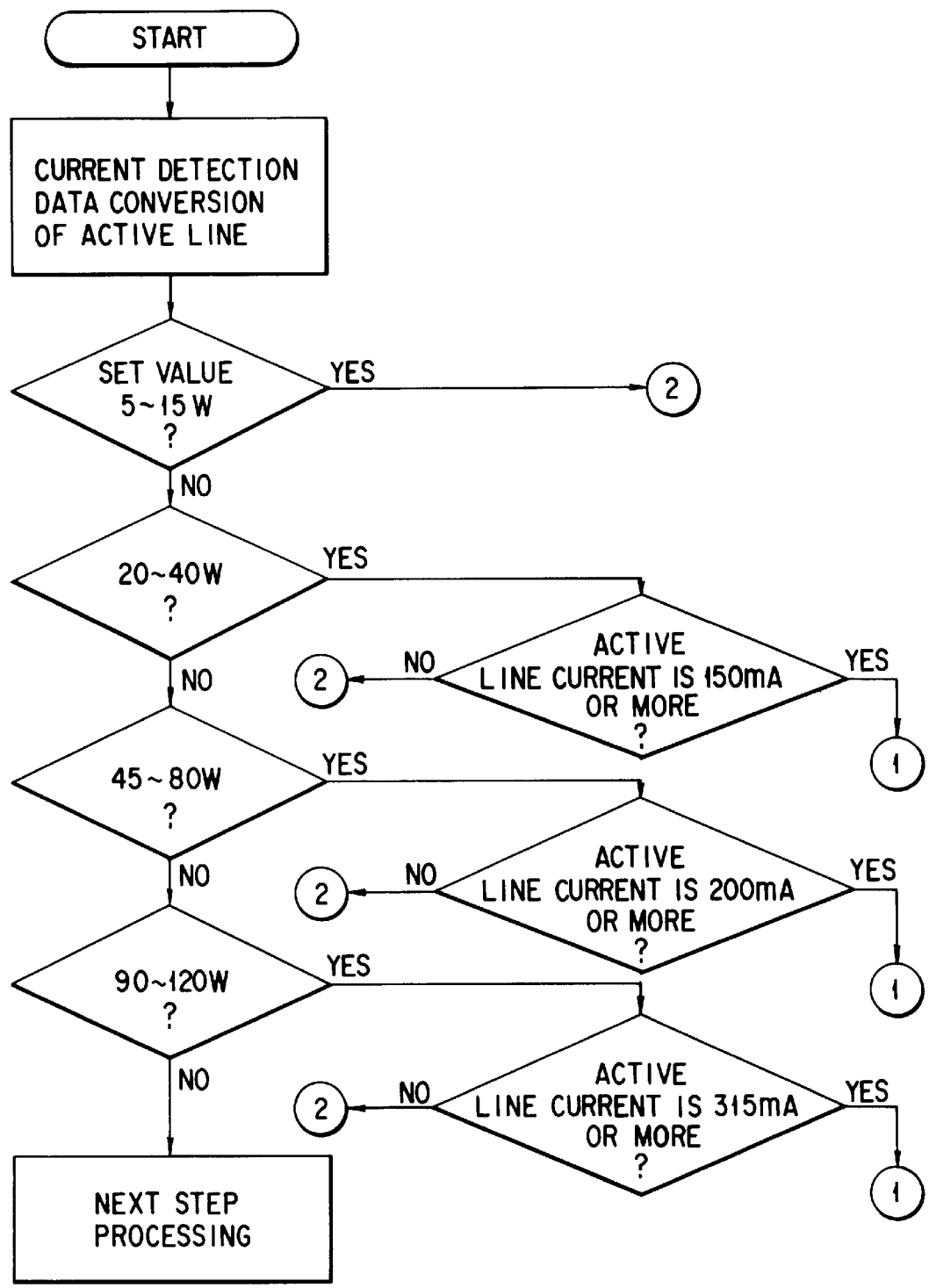
FIG. 18 is a flow chart of data processing in the electric operation apparatus according to the third modification of the second embodiment.

The processing flow of digital data taken in by the control section 161 is shown in FIGS. 18, 19A and 19B. At first, a current flowing through the active line 171 is detected and data conversion is performed. Then, the data is read and stored into a memory. Further, the converted data and a predetermined arc detection threshold level are compared with each other. If the data thus taken in is equal to or smaller than the threshold level, arc discharging does not take place, and therefore, the output circuit 167 determines it as an open circuit state, and intermittently sends a waveform selection signal supplied from the control section 161, at a repetition frequency (to an intermittent output processing routine 2 shown in FIG. 19B). Further, if the data thus taken in is equal to or greater than the threshold level, it is determined that arc discharging starts at an output end, i.e., that the output circuit 167 becomes a closed circuit, and a waveform selection signal is continuously sent from the control section 161 (to a continuous output processing routine 1 of FIG. 19A). In this manner, when the output circuit 167 is an open circuit, the effective value of the output voltage can be greatly reduced while maintaining the releasing voltage at the output end to be high. That is, it is possible to reduce the high frequency leakage current while maintaining a releasing voltage high enough to cause a breakdown in the air. Further, when the output circuit 167 is a closed circuit, arc discharging at an output end can be stably maintained since a waveform selection signal is continuously outputted.

Here, to decide the threshold level for determining the arc condition, the following respects must be considered. Specifically, when the output setting value is low, or when the impedance of an organism tissue 175 is very high, the current flowing through the output circuit 167 is very small. In this case, even though the output circuit is in a closed circuit state, it is determined that the output end is released, and an output waveform is incorrectly suppressed. Then, a power according to a setting value is not outputted. Therefore, in order to prevent such a situation, the threshold level for determining the arch state must be set to a level which differs in accordance with the output setting value set in the step shown in FIG. 18.

In this modification, the arc state at the output end is detected by detecting a current flowing through the active line 171. However, the arc state can be detected by detecting the current flowing through the counter plate line 172. A very high voltage is applied to the active line 171 side, in comparison with the ground. The noise level is very high. Therefore, a detection signal used for determining the arc state is easily effected by noise, and stable suppression control cannot be performed. Meanwhile, the counter plate line 172 has an electric potential very close to the ground level, and the noise level is very small. Further, there is a very large difference between when arc discharging occurs at the output end and when arc discharging does not occur. Therefore, it is possible to obtain a large noise margin, so that the threshold level can be set such that a high frequency power as expected is outputted even when the impedance of the organism tissue 175 is high or when the output setting value is small.

As a result of this, in spray coagulation in which a high frequency leakage current is generated most easily, the state of the arc discharging can be observed on real time, and the output waveform is controlled, depending on the state observed. Therefore, a high frequency leakage current is reduced while maintaining a releasing voltage necessary for causing a breakdown, so that a treatment can be carried out more safely and securely.

According to the second embodiment described above, since an endoscopic treatment using an endoscope code system and a surgical operation can be performed with one signal apparatus, not only very convenient electric surgical operation apparatus can be provided but also monitor methods are respectively provided for different techniques, with respect to a high frequency leakage current which is disadvantageous when using the electric surgical operation apparatus, so that erroneous operation is not caused but secure determinations and treatments can be realized.

Figure 20:
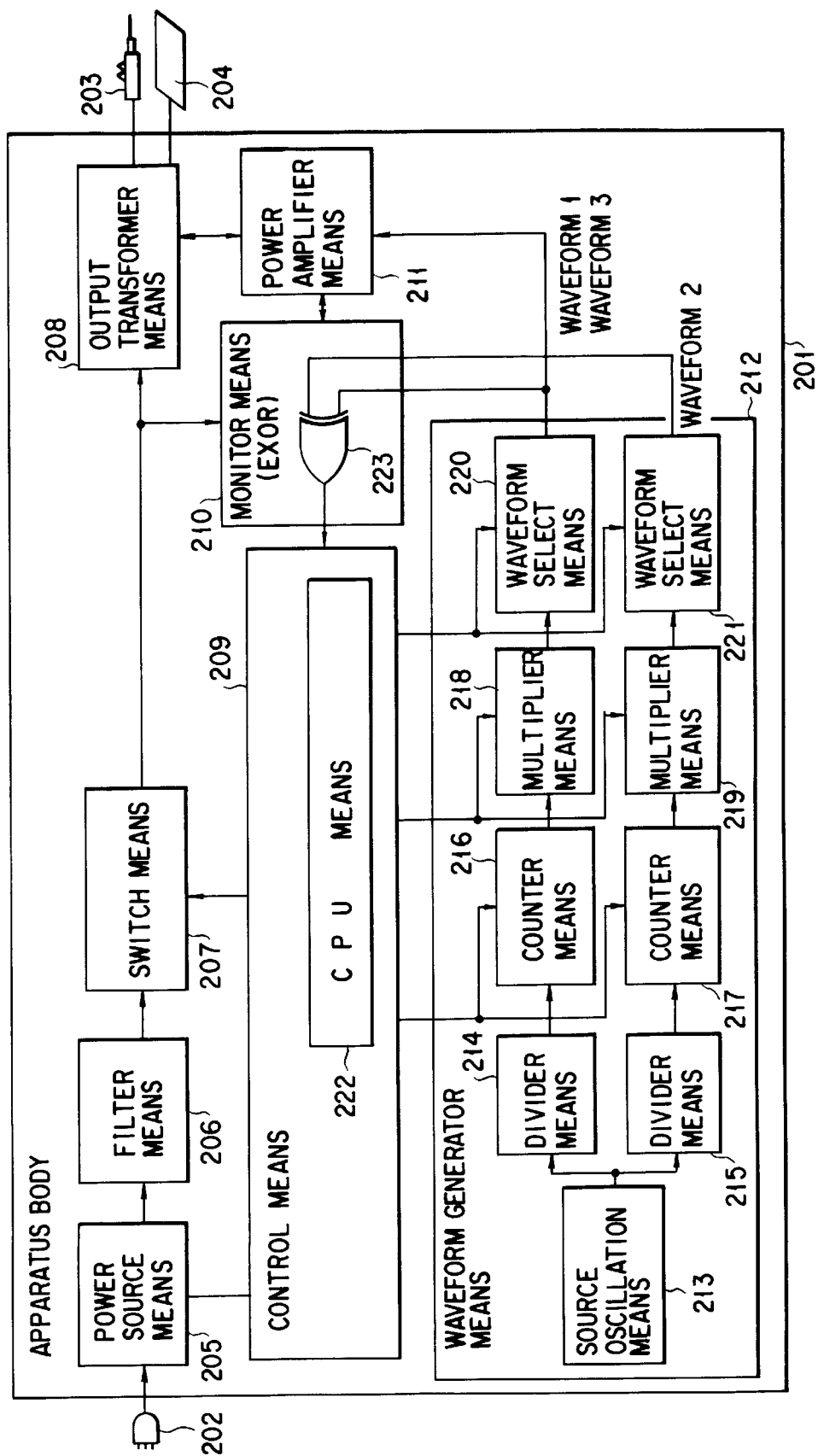
FIG. 20 is a view showing the structure of the third embodiment.

In the following, a third embodiment of the present invention will be explained. FIG. 20 shows a structure of the third embodiment. As an external structure, the body 201 of the electric knife apparatus as an electric operation apparatus is connected to a power source code 202 for supplying the apparatus body 201, an electric knife hand piece 203 for performing a treatment on a patient on the basis of a high frequency signal outputted from the electric knife apparatus body 201, and a counter plate 204.

In the following, the internal structure the electric knife apparatus body 201 will be explained. A control means 209 for performing control of respective means described below includes a CPU means 222. A waveform generator means 212 for generating a waveform divides a source oscillation signal generated by the source oscillation means 213 by n times with use of a divider means 214, and is divided again by a counter means controlled by the CPU means 222. A multiplier means 218 multiplies the division wave generated by the counter means 216, thereby to generate various waveforms. Further, the waveform generated by the multiplier means 218 is selected by the waveform selection means 220 controlled by the CPU means 222. In addition, the waveform generator means 212 performs the same operation as described above by means of a divider means 215, a counter means 217, a multiplier means 219, and a waveform selection means 221.

In addition, the power source means 205 generates a DC voltage from a commercial power source supplied through a power source code 202, and supplies the voltage to a filter means 206 and a switch means 207. The DC voltage described above is applied to an output transformer means 208 and a power amplifier means 211. The power amplifier means 211 performs switching amplification by means of a waveform selected by the waveform selection means 220. A monitor means comprising an EXOR circuit 223 subjects two waveforms generated by the waveform generator means 212, to a logic calculation, and sends the calculation result to the control means 209.

The operation of the third embodiment described above will be explained below.

In the waveform generator means 212, a certain waveform is generated by a source oscillation means 213, a divider means 214, a counter means 216, a multiplier means 218, and a waveform selection means 220, and the waveform is referred to as a waveform 1 in the following explanation. In addition, another certain waveform is generated by a source oscillation means 213, a divider means 215, a counter means 217, a multiplier means 219, and a waveform selection means 221, and this waveform is referred to as a waveform 2, in the following explanation.

Figure 24A:
FIGS. 24A, 24B, and 24C are views showing two waveforms generated by a waveform generator means and a first example of an output waveform generated by an EXOR circuit according to the third modification.
Figure 24B:
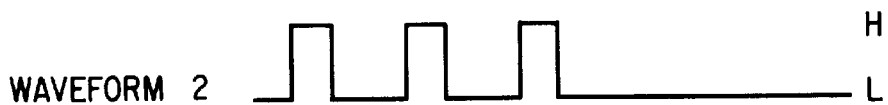
Figure 24C:
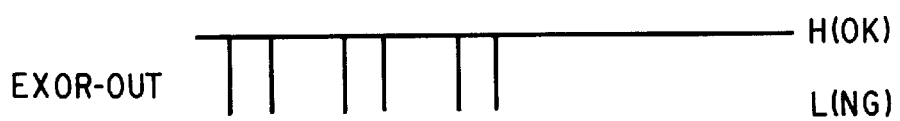

FIGS. 24A, 24B, and 24C show the waveforms 1 and 2 described above and a waveform of an EXOR-out as an output from an EXOR circuit 223 where "H" denotes a normal state and "L" denotes an abnormal state. From these figures, it is determined that the EXOR-out is "H" and is normal since the waveforms 1 and 2 are of a same waveform.

Figure 25A:
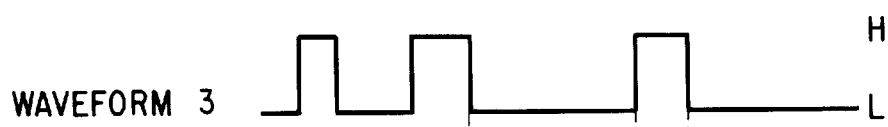
FIGS. 25A, 25B, and 25C are views showing two waveforms generated by a waveform generator means and a second example of an output waveform generated by an EXOR circuit according to the third modification.
Figure 25B:
Figure 25C:

Here, when at least one of the divider means 214, counter means 216, multiplier means 218, and waveform selection means 220 is defective, there is a case in which the waveform 1 is deformed into an unintended shape as shown as a waveform 3 and is then outputted. In this state, the EXOR-OUT is as shown in FIG. 25C. Specifically, the EXOR-OUT is "H" where the waveforms 2 and 3 are of one same waveform, while the EXOR-OUT is "L", i.e., abnormal where the waveforms 2 and 3 are different from each other. The output result of the EXOR circuit 223 is transmitted to the control means 209, and the switch means 207 is controlled to stop outputting. Here, the output can be stopped by controlling the power source means 205. In addition, it is possible to stop the output by controlling the waveform generator means 212.

According to the third embodiment as described above, it is possible to prevent an unintended waveform from being transmitted to an output transformer means and a power amplifier means and from being outputted as a high frequency output, when at least one means of the wave generator means 212 is defective and causes an erroneous operation.

Figure 21:
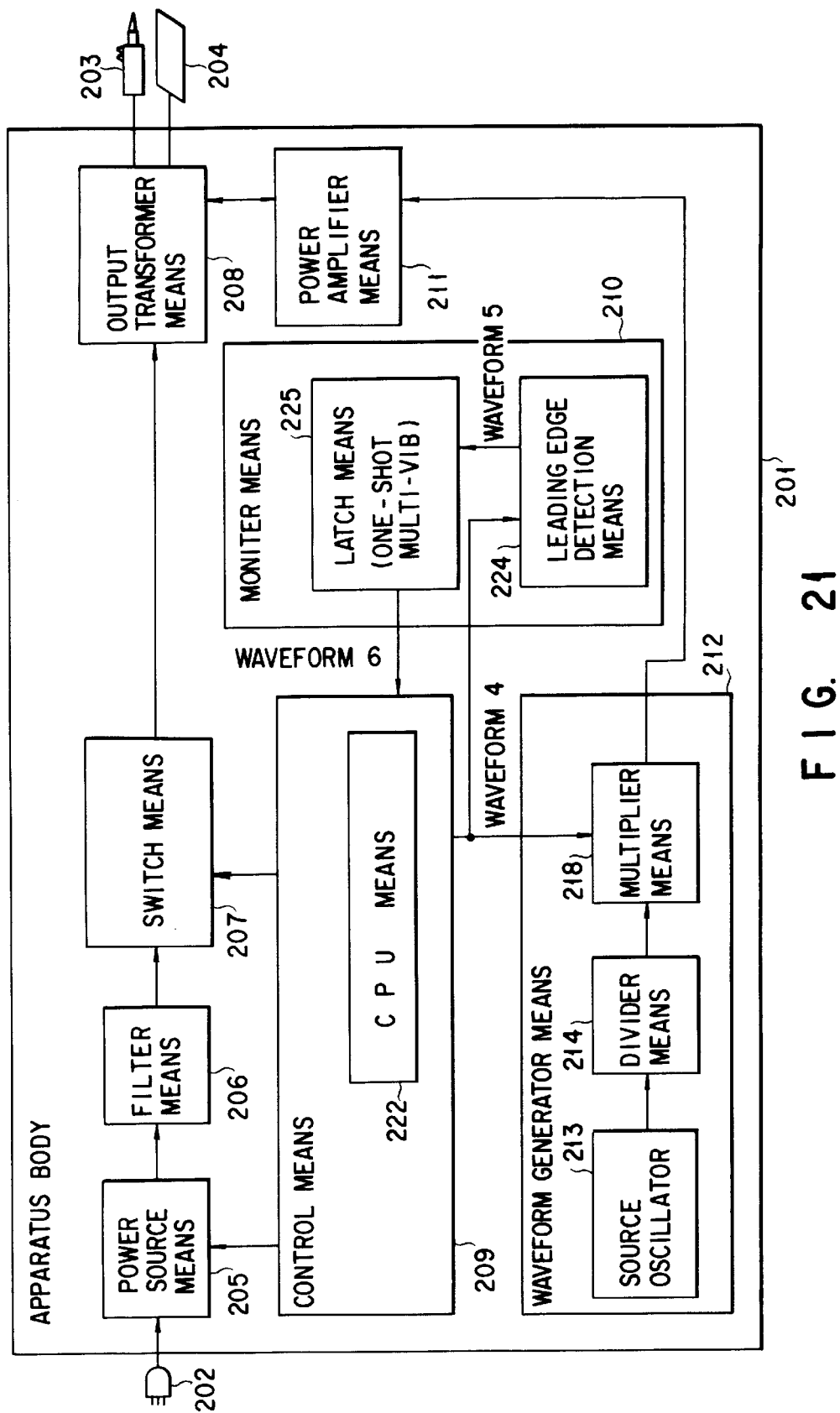
FIG. 21 is a view showing the structure of a first modification according to the third embodiment.

In the following, a first modification of the third embodiment described above will be explained. FIG. 21 shows a structure of this modification. The external structure is the electric operation apparatus body 21 is the same as that of the third embodiment.

The internal structure will be explained below. A control means 209 for controlling respective means comprises a CPU means 222. The waveform generator means 212 comprises a source oscillation means 213, a divider means 214, and a multiplier means 218. A source oscillation signal generated by the source oscillate means 213 is divided by n through the divider means 214, and thereafter, is multiplied by a waveform transmitted from the CPU means 222 by the multiplier means 218.

A DC voltage generated by a power source means 205 is applied to an output transformer means 208 and a power amplifier means 211 through a filter means 206 and a switch means 207. The power amplifier means 211 receives a waveform generated by a waveform generator means 212 and performs switching amplification. The monitor means 210 comprises a leading edge detection means 224 and a latch means 225 for holding an output result for a predetermined time period.

A waveform signal inputted into the multiplier means 218 is also inputted into a leading edge detection means 224 by the CPU means, and a leading edge of the waveform signal is detected. With use of a detection result, the latch means 225 is controlled. Then, the output state after the CPU means 222 starts transmitting a waveform is transmitted to the CPU means 222.

In the following, operation of the first modification described above will be explained. A waveform inputted into both the multiplier means 218 and the leading edge detection means 224 is referred to as a waveform 4. In addition, a waveform inputted from the leading edge detection means 224 to the latch means 225 is referred to as a waveform 5. A waveform inputted from the latch means 225 into the CPU means 222 is referred to as a waveform 6.

FIGS. 26A, 26B, and 26C respectively show waveforms 4, 5, and 6 when the wave form is a continuous wave. FIGS. 27A, 27B, and 27C respectively show waveforms 4, 5, and 6 when the wave form is a burst wave. FIGS. 28A, 28B, and 28C respectively show waveforms 4, 5, and 6 when the wave form is a mixed wave. In case of FIGS. 26A, 26B, and 26C, in response to an input of a waveform 4, the leading edge detection means 224 outputs a waveform 5 which has only one wave crest. The latch means 225 performs a series of operations such that a waveform which maintains "H" only for a predetermined time t1 is outputted in response to the leading edge of the waveform 5.

In case of FIGS. 27A, 27B, and 27C, the leading edge detection means 224 outputs a waveform 5 which is a waveform including continuous wave crests, in response to an input of the waveform 4, like the above cases. In this case, the latch means 225 receives the leading edge of the waveform 5 and outputs "H" for a predetermined time t1, thereby to become nearly "L". However, after t2, a next leading edge is inputted, and from this time point, the output becomes "H", again, for only a time period of t1. This operation is repeated continuously, the latch means 225 maintains "F" at all, after the output has once become "H".

The mixed waves shown in FIGS. 28A, 28B, and 28C are operated in the same manner as described above. However, since the waveform 5 as an output from the leading edge detection means 224 does not have a next leading edge within a time t1 from the third wave crest, the waveform 6 as an output from the latch means 225 cannot maintain "H", at last, and returns to "L".

Here, the waveforms 6 as output waveforms of the latch means 225 are compared between the FIGS. 26A, 26B, and 26C, FIGS. 27A, 27B, and 27C, and FIGS. 28A, 28B, and 28C, and it is found that a determination point A after T1 from when a waveform 4 is outputted from the CPU means 222 and a determination point B after T2 therefrom are different between these figures. Therefore, if the determination points A and B of the waveforms 6 are detected by the CPU means 222, it can be determined whether or not the waveform 6 is of a type equal to an intended waveform. Then, if the waveform 6 is abnormal, the output is stopped by controlling the switch means 207 by means of the control means 209.

According to the first modification of the third embodiment, even if the waveform generator means 212 is not constructed so as to have double structures, waveforms can be monitored, and the amount of equipment can be reduced.

Figure 22:
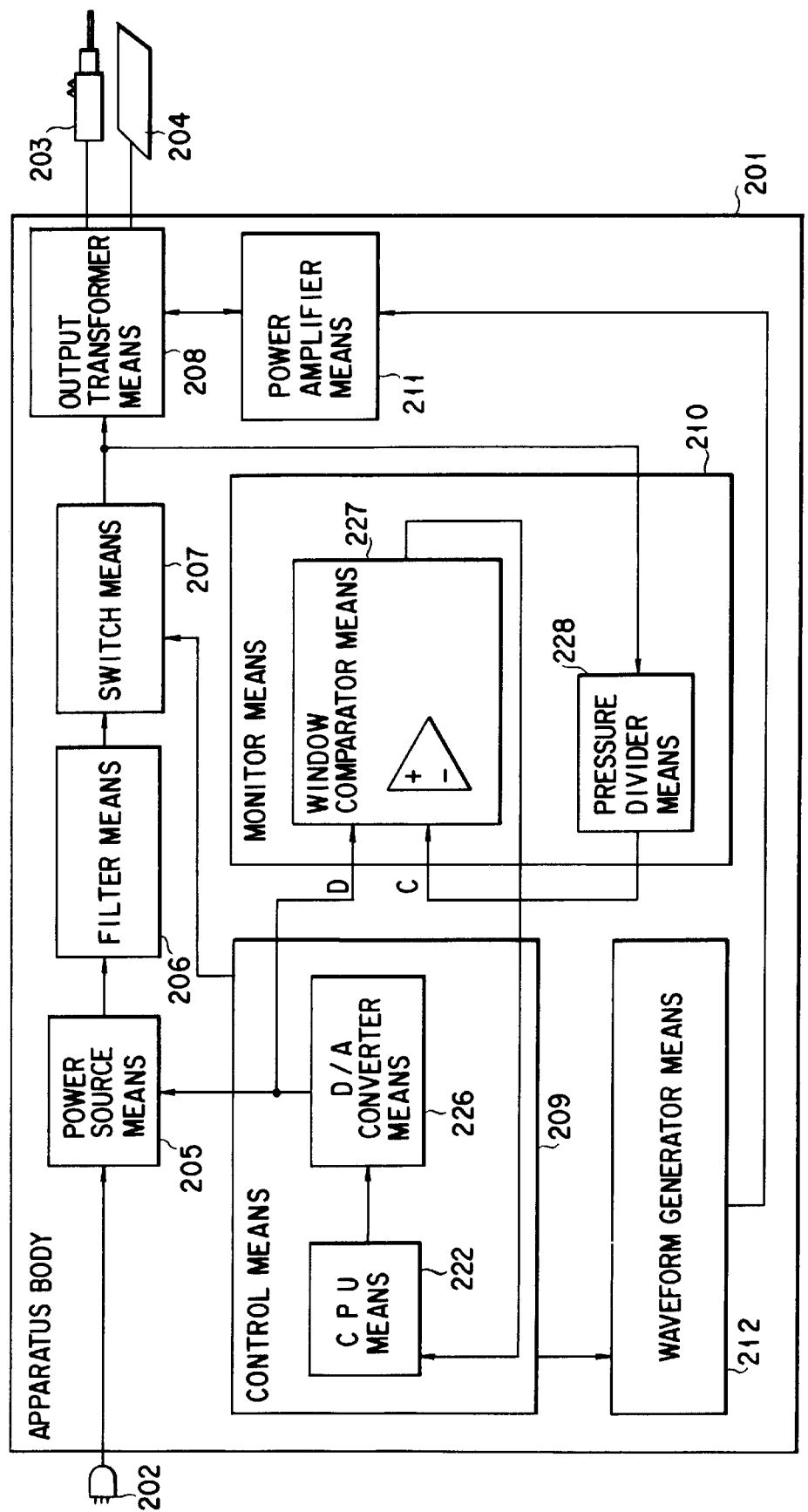
FIG. 22 is a view showing the structure of a second modification according to the third embodiment.

In the following, a second modification of the third embodiment will be explained. FIG. 22 is a view showing the structure of the second modification. The external structure of the electric operation apparatus body 201 is the same as that of the first modification.

In the following, the internal structure will be explained. The control means 209 comprises a CPU means 222 and a D/A converter means 226, and a digital signal transmitted by the CPU means 222 is analogue-converted by the D/A converter means 226. The D/A converter means 226 is connected to a power source means 205, and this power source means 205 generates a DC voltage which is N times as high as an analogue signal inputted from the D/A converter means 226. Here, the D/A converter means 226 may be constituted by a plurality of circuits.

In addition, the monitor means 210 comprises a window comparator means 227 and a voltage divider means 228, and a DC voltage from the power source means 205 is transmitted to the voltage divider means 228 through a filter means 206 and a switch means 207, and is divided into 1/N voltages. One of two inputs to the window comparator means 227 is inputted from the D/A converter means 226, the other is a voltage divided by N by the voltage divider means 228.

In the following operation of the second modification will be explained.

The output of the D/A converter means 226 is connected to two means, one of which is a power source means 205. Here, if an analogues signal outputted from the D/A converter means 226 is X[V], the power source means 205 generates a DC voltage multiplied by N, and apply this voltage to an output transformer means 208 and a power amplifier means 211 through a filter means 206 and a switch means 207. This DC voltage is also applied to the voltage divider means 228, and is divided into 1/N voltages. A divided voltage of 1/N is thereafter inputted into one input of the window comparator means 227. This voltage is referred to as C[V].

In addition, another output of the D/A converter means 226 is directly inputted into the window comparator means 227. This voltage is referred to as D[V]. Where an error coefficient of the power source means 205 is α and an error coefficient of the voltage divider means 228 is β, the following relation is satisfied.

$$C = X \cdot N \cdot \alpha \cdot (1/N) \cdot \beta = \alpha \cdot \beta \cdot X$$

$$D = X$$

Here, the window comparator means 227 compares C and D with each other within a range which means, for example, whether or not a deviation is within a range of ±20% with D taken as a standard. In this modification, if the deviation is a value out of the range of ±20%, the condition is determined as abnormal, and an abnormality signal is transmitted to the control means 209, and the switch means 207 is controlled thereby to stop the output.

According to the second modification described above, whether or not deviation of the DC output of the power source means 205 from a desired output is greater than a predetermined range is monitored. If abnormality appears, a high frequency output is stopped. Therefore, a malfunction and an erroneous operation in each means from the power source means 205 to the pressure divider means 228 can be detected with a simple structure. In addition, a malfunction and an erroneous operation of the D/A converter means 226 can be detected in a manner in which the D/A converter is arranged to have double structures, so that an analogue signal is made independent and is inputted into the power source means 205 and the window comparator means 227.

Figure 23:
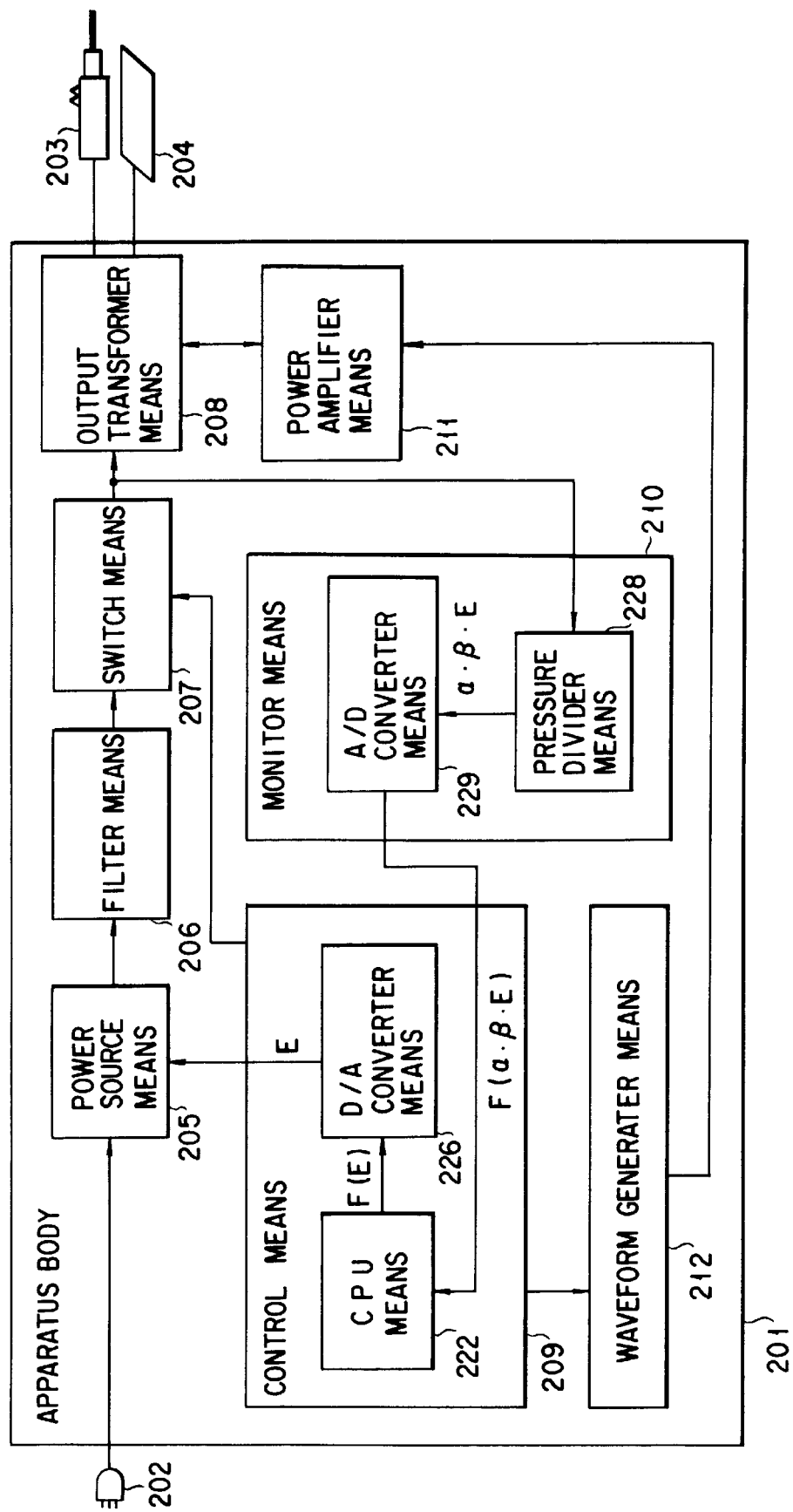
FIG. 23 is a view showing the structure of a third modification according to the third embodiment.

In the following, a third modification of the third embodiment. FIG. 23 shows a structure of the third modification. The external structure of the electric operation apparatus body 201 is the same as that of the third embodiment.

The internal structure thereof will be explained below. The control means 209 comprises a CPU means 222 and a D/A converter means 226. A digital signal inputted by the CPU means 222 is converted into an analogue signal and is transmitted to the power source means 205. The power source means 205 generates a DC voltage as N times large as an analogue signal outputted from the D/A converter means 226.

The monitor means 210 comprises an A/D converter means 229 and a pressure divider means 228. A DC voltage generated by the power source means 205 is inputted into the pressure divider means 228 through a filter means 206 and a switch means 207, and is divided into voltages of 1/N. A divided voltage of 1/N is inputted into the A/D converter means 229 and is converted into a digital signal, which is then transmitted to the control means 209.

In the following, the operation of the third modification described above will be explained.

When a digital signal F(E) which makes the analogue signal as an output of the D/A converter means 226 to be E[V] is outputted from the CPU means 222, the power source means 205 generates a DC voltage which is N times as large as the E[V]. The DC voltage is supplied to the output transformer means 208, the power amplifier means 211, and the voltage divider means 228 through the filter means 206 and the switch means 207. The inputted DC voltage is divided by the voltage means 228 into voltages of 1/n, and thereafter, divided voltages are digital-converted by an A/D converter means 229. Here, an analogue signal inputted into the A/D converter means 229 is referred to as G. Where an error coefficient in the power source means 205 is α and an error coefficient of the voltage divider means 228 is β, the following relation is satisfied.

$$G = E \cdot N \cdot \alpha \cdot (1/N) \cdot \beta = \alpha \cdot \beta \cdot E$$

Specifically, a digital signal outputted as F(E) from the CPU means becomes an analogue signal expressed as α·β·E, and is inputted into the A/D converter means 229. The A/D converter means 229 transmits a digital signal expressed as F(α·β·E) to the CPU means 222. The CPU means 222 calculates and compares F(E) with F(α·β·E), thereby to determine whether or not F(α·β·E) is within a predetermined range relative to F(E), e.g., whether or not the deviation is within a range of ±90%. If the deviation is out of the range, the switch means 207 is controlled by the control means 209, thereby to stop the output.

According to the third modification as described above, the range in which two digital signals of F(E) and F(α·β·E) are calculated and compared with each other can be broadened or narrowed with ease by changing programs. In addition, in the electric knife apparatus, it is well known that high frequency outputs of various waveforms are obtained. If the range should be changed for each of waveforms, the range can be changed without additionally provide a circuit.

According to the third embodiment described above, the apparatus is arranged such that a waveform generated by the waveform generator means is monitored, and therefore, it is possible to prevent generation of an unexpected output due to a malfunction and an erroneous operation of the waveform generator means, thereby to improve the safety in an operation.

In the following, a fourth embodiment of the present invention will be explained.

FIGS. 29 to 31 are related to the fourth embodiment of the present invention. FIG. 29 is a view for explaining the structure of a main part of an electric operation apparatus, and FIG. 30 is a view for explaining the output characteristic of an internal transformer provided in an output circuit. FIG. 31 is a characteristic graph of a high frequency output from the output circuit.

As shown in FIG. 29, the electric operation apparatus 305 comprises a high frequency cautery power source device 306 (which will be referred to as a cautery power source hereinafter) and a treatment tool 307 consisting of, for example, a mono-polar treatment tool 371 connected to a mono-polar port 360a of the cautery power source 306 and a patient electrode 372 connected to a counter plate port 360b.

The cautery power source 306 comprises a high frequency power amplifier circuit 361 for high-frequency amplifying a waveform signals which bases high frequency powers corresponding to treatments such as incision, mixture, coagulation and the like and which are generated by a waveform shaping circuit (not shown) positioned in a front stage, an output circuit 362 constituted so as to output a high frequency power amplified by the high frequency power amplifier circuit 361 through three internal transformers, a relay circuit 363 for switching and supplying the high frequency powers outputted from the internal transformers of the output circuit 362 to the treatment tool 307, a sensor 364 as a monitor means which is provided between the relay circuit 363 and the ports 360a and 360b and which is used for monitoring an output voltage from a cautery power source, an output current, a feedback current, a electrostatic capacity of an organism, and an organism impedance, and an A/D converter 365 for digital-converting an signal outputted from the sensor 364, and a CPU 366 which is connected to the A/D converter 365, the high frequency power amplifier circuit 361, and the relay circuit 363 and which controls respective circuits.

As shown in FIG. 30, three internal transformers are respectively set in such three setting conditions in which the output characteristics of the setting conditions respectively have peaks when the value of the organism impedance is within a range a, when this impedance is within a range b, and when this impedance is within a range c, where the maximum output value of the high frequency power is set to 150 W or 300 W.

The CPU 366 is inputted with a detection signal of the organism impedance detected by the sensor 364, through the A/D converter 365, and selects an internal transformer which outputs a high frequency power corresponding to the organism impedance, from the output circuit 362, thereby switching the relay circuit 363 so as to supply an output to the treatment tool 371, for example. Thus, the CPU 366 is arranged so as to perform selection of various waveforms, control of control values of various circuits, and the like, or so as to perform abnormality notification through a notification means or stop the output, when control values of various circuits must be controlled or when an abnormal condition occurs.

Since the electronic operation apparatus 305 is arranged in a structure as described above, the apparatus is arranged so as to detect an output voltage and an organism impedance as a change in organisms, by means of the sensor 364, when a treatment is performed with use of this electric operation apparatus 305. Then, a change in organism impedance is continuously fed back to and is grasped by the CPU 366. Therefore. The relay circuit 363 is continuously controlled by the CPU 366 and a high frequency power of an optimum value is outputted from an internal transformer of the output circuit 362. As a result of this, high frequency powers outputted through the relay circuit from the output circuit including internal transformers having three different output characteristics are controlled by the CPU 366, so that a substantially flat maximum output value to be outputted, within a range in which the organism impedance is, for example, within a range of 200Ω to 500Ω even through one transformer has only one output characteristic of damping as indicated by a broken line, as shown in FIG. 31. Hence, treatments such as incision, coagulation, and the like can be performed while attaining a high output.

Note that the number of internal transformers provided in the output circuit 362 is not limited to three, but may be two, four or more. If internal transformers are chosen and provided in view of the organism impedance and if the relay circuit 363 is switched by the CPU 366 on the basis of a detection signal of the organism impedance detected by the sensor 364 so that the high frequency output of a desired one of the internal transformers is outputted, controls suitable for user environments can be attained, e.g., a high frequency power can have a waveform which is chosen with coagulation being taken more significant than incision starting, as shown in FIG. 32, or such a waveform can be chosen for the high frequency output which makes a peak value be outputted when starting incision, as shown in FIG. 33, so that the cutting quality is improved and which also makes a peak value be outputted again when incision is almost finished, so that the stanching ability is improved.

Thus, by switching the relay circuit which connects internal transformers of the output circuit for outputting a high frequency power in accordance with an organism impedance detected by a sensor, user environments which a user will require can be controlled by the CPU.

Meanwhile, a conventional electric operation apparatus is arranged so as to continuously output a high frequency power while a switch section such as a foot switch, a surgical hand piece (which will be referred to as a hand piece hereinafter) whose output is operated by hands, or a hand switch which is used to perform only control of the output by hands in place of the foot switch is turned on. In addition, in an electric operation which is carried out with use of a conventional endoscope, a relatively short output time is repeated to carry out the electric operation. However, in several cases, a treatment is performed with an elongated conductive time period. Further, due to a malfunction of the electric operation apparatus itself, or due to a defect such as a defective connection or the like between a cautery power source and a treatment tool, there has been a case in which a high frequency power does not perfectly flow from a treatment tool to an organism. Thus, if a high frequency power is not supplied to a treatment tool but if a high frequency power is continuously generated, heat may be generated in a cautery power source, or a defect may occur and the durability may be degraded.

Therefore, in order to overcome these problems, whether a switch such as a hand piece 381, a foot switch 382, a hand switch or the like not shown in an electric operation apparatus 305a as shown in FIG. 34 is turned on or off is detected by a switch detection section 384, and a signal detected by the switch detection section 384 is transmitted to the CPU 366 while changes in organism impedance are monitored by the sensor 364 of the embodiment described above, so that whether or not outputting of a high frequency power from a treatment tool is started is detected.

Figure 35:
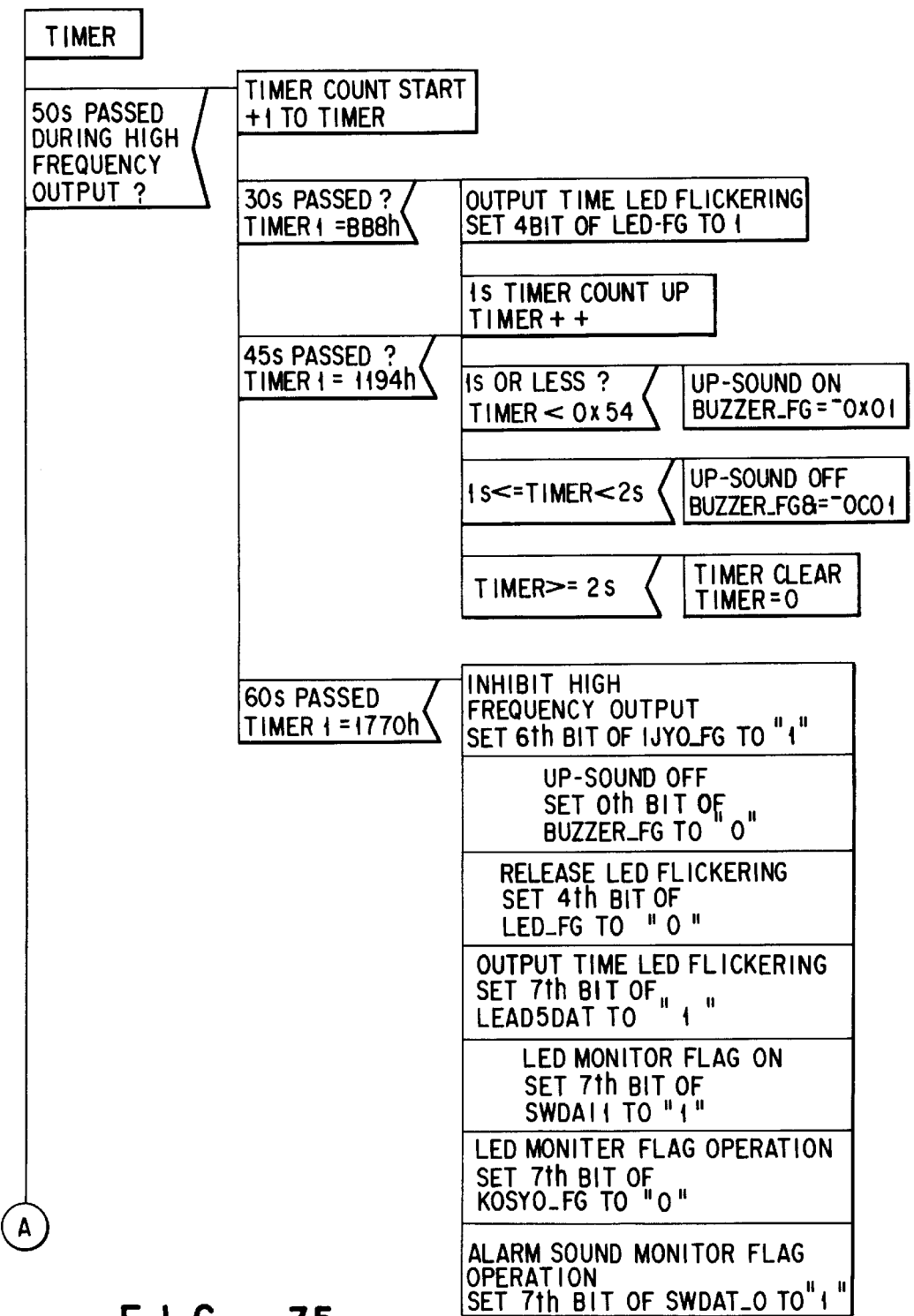
FIG. 35 is a safety management setting table (1)
Figure 36:
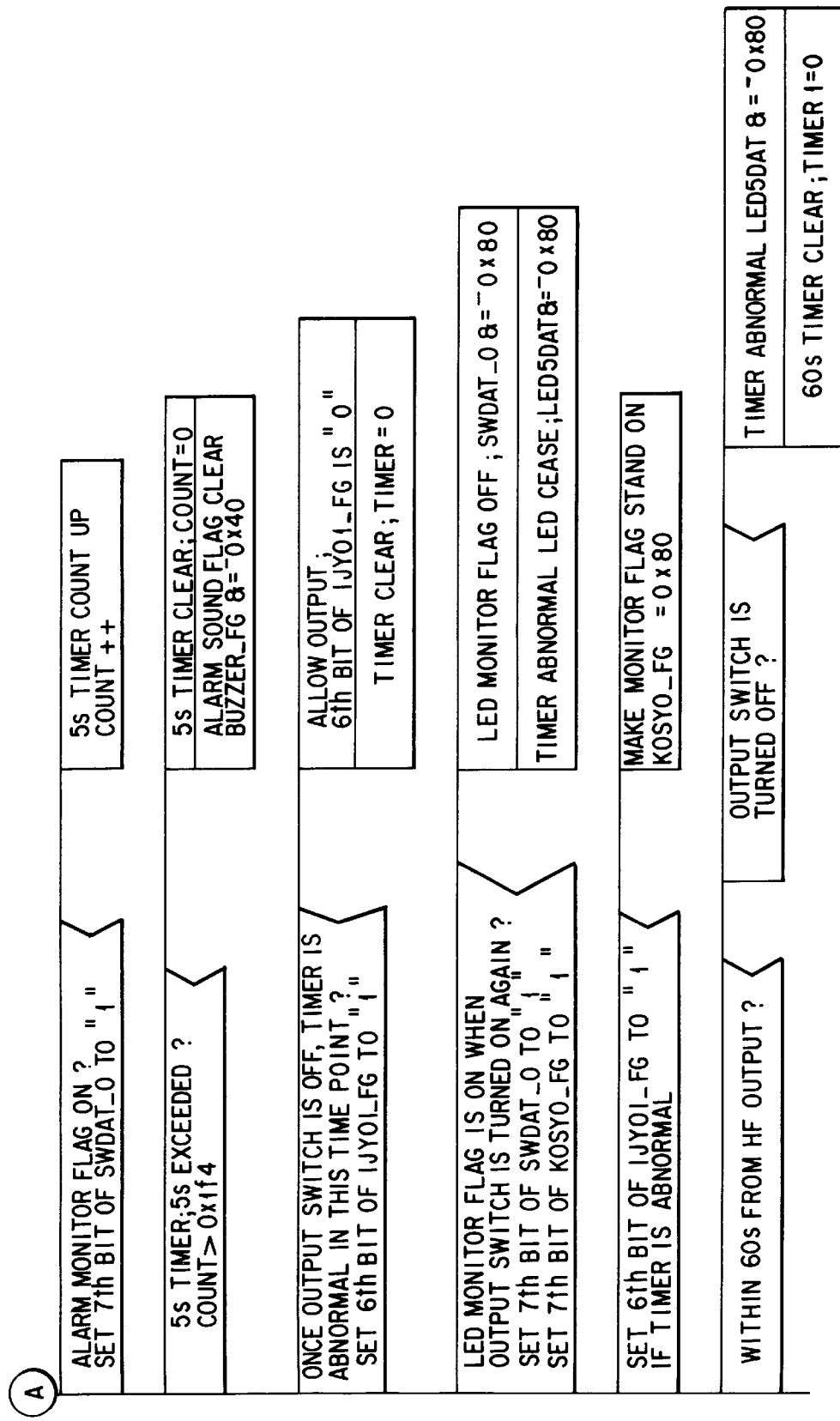
FIG. 36 is a safety management setting table (2)

Specifically, in the electric operation apparatus according to this embodiment, once outputting of a high frequency power is started, a continuous output time is measured for at least one of the time previously set in the apparatus body and the time set afterward by a main panel. Further, visual display is performed with use of an LED or the like as a notification means or notification is issued by activating a buzzer or the like, for every term of elapsed time, for example, as shown in setting tables of FIGS. 35 and 36. Note that measurement of the elapsed time is performed by a micro processor, a counter element, or a timer element.

For example, if a breakdown occurs in a treatment tool, a high frequency current does not flow through human organisms but only the cautery power source is brought into a continuous output condition when the foot switch is turned on. In this state, the turning-on state of the switch is confirmed by the switch detection section 384, while changes in organism impedance are not detected by the sensor 364 since a high frequency power acts on organism tissues. Therefore, as shown in Step S1, an LED is made flicker when 30 seconds have passed. Further, every time when a predetermined time has passed, the processing goes to a new step and a predetermined operation is carried out. In this manner, a user can be notified of an abnormal condition, and a breakdown and degradation in durability due to heat of a cautery power source in durability can be prevented.

In addition, not only whether an output switch is turned on or off is detected, but also whether or not a high frequency current is applied to an organism tissue can be detected from changes in organism impedance. Therefore, it is possible to make such an arrangement which enables time measurement from when a current actually flows to an organism tissue.

Note that operations shown in the setting tables are previously set in the machine body, and therefore, changes concerning elapsed times and notification means can arbitrarily set.

Figure 37:
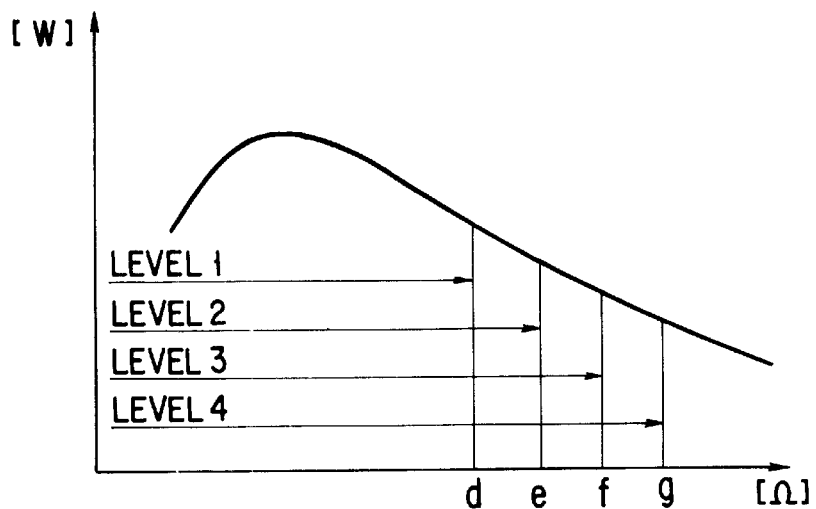
FIG. 37 is a view showing a relationship between an organism impedance and a threshold value.

In addition, for example, as shown in FIG. 37, threshold values of levels 1 to 4 are set, depending on values d, e, f, and g of organism impedances. Further, when the organism impedance reaches to a previously set threshold value while an electric operation is performed, the sensor 364 detects that the impedance reaches the threshold value, and transmits a detection signal thereof to the CPU 366, thereby automatically stopping the high frequency output from the cautery power source 306 to the treatment tool. Thus, coagulation quality or incision quality required by a user can be set.

In addition, since a user can select and set a level in compliance with a portion to be treated in an operation, a technique to be adopted, a treatment tool to be used, or the like, coagulation quality and incision quality which continuously ensures excellent reproductivity can continuously be obtained. Therefore, it is not necessary to perform a cut and try procedure as has been carried out every time an operation is performed in a conventional electric operation apparatus in order to set the output to a value suitable for an operation, and the operation time can be shortened and the efficiency is increased.

Note that the value to be detected by the sensor is not limited to an organism impedance, and but may be an electrostatic capacity of an organism, an output power, or an output current. In addition, although explanation has been made with respect to an electric operation apparatus using a treatment tool of a mono-polar mode, a treatment tool may be one of a bipolar mode.

Figure 38A:
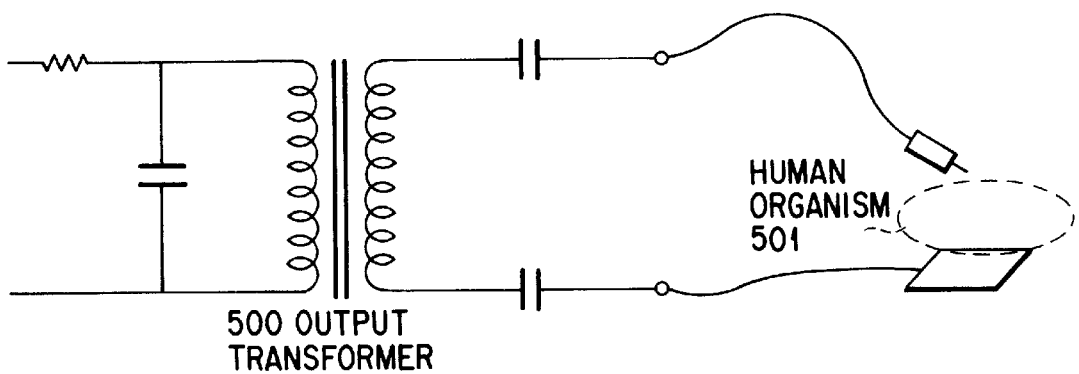
FIGS. 38A and 38B are views for explaining a modification of the fourth embodiment of the present invention.
Figure 38B:
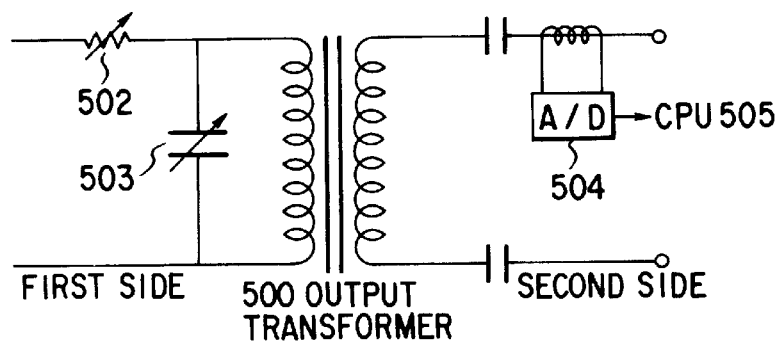

FIGS. 38A and 38B are views for explaining modifications of the fourth embodiment as described above.

An output circuit having an output transformer 500 in a conventional electric knife has a structure shown in FIG. 38A, and apparent impedances are about 300 to 500Ω in case of a mono-polar type and about 100Ω in case of a bipolar type. These values are specific to the circuit and are fixed values. However, since the impedance of a human organism 501 varies, the output of the output circuit changes as the impedance changes.

FIG. 38B shows a modification which solves the problem as described above. In this example, the output voltage in the second side of the output power source of the output transformer 500 in the output circuit and is fed back to the CPU 505 through the A/D converter means 504. The CPU 505 drives a variable resistor 502 and a variable controller 503 in accordance with an output voltage value detected, and changes an apparent impedance of the output circuit, so that an output characteristic can be obtained in compliance with the human organism 501.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An electric operation apparatus for performing a high frequency treatment on organic tissue, comprising:

selection means for selecting one of a plurality of high frequency output modes, said plurality of high frequency output modes including a spray coagulation mode in which a high releasing voltage is generated so that a breakdown is induced in air to thereby cause arc discharging at an output end, and so that a coagulation effect is generated by a high frequency current which flows when the arc discharging occurs, even though the organic tissue being treated is not in contact with an active electrode;

high frequency generator means, including a waveform generator section for generating waveforms corresponding to respective modes of the plurality of high frequency output modes, for outputting high frequencies corresponding to respective waveforms;

control means for controlling the high frequency generator means in accordance with selection operations performed by the selection means;

an active line connected to the high frequency generator means and including an active electrode;

a counter plate line connected to the high frequency generator means and including a counter plate; and monitor means for detecting a current value of the high frequency current which flows between the active line and the counter plate line when the spray coagulation mode is selected by the selection means, and for inputting the current value into the control means;

wherein said control means further comprises:

means for holding in advance a threshold value at which the arc discharging is generated at the output end;

means for comparing the current value input by the monitor means and the threshold value, when the spray coagulation mode is selected by the selection means;

means for determining whether arc discharging has occurred at the output end, based on a result of the comparison; and means for (i) controlling the high frequency generator means to continuously output a waveform corresponding to the spray coagulation mode generated by the waveform generator section if arc discharging at the output end is detected based on the result of the comparison, and (ii) controlling the high frequency generator means to intermittently output at a predetermined cycle a waveform corresponding to the spray coagulation mode generated by the waveform generator section if arc discharging at the output end is not detected based on the result of the comparison.

2. The electric operation apparatus according to claim 1, wherein said monitor means includes means for detecting a current flowing through the active line.

3. The electric operation apparatus according to claim 1, wherein said monitor means includes means for detecting a current flowing through the counter plate line.

4. An electric operation apparatus according to claim 1, further comprising setting means for setting a high frequency output value output by the high frequency generator means,
wherein said control means further comprises means for holding a plurality of threshold values corresponding to the high frequency output value set by the setting means, and
wherein said control means compares the current value input by the monitor means and the threshold value corresponding to the high frequency output value set by the setting means.

* * * * *

UNITED STATES PATENT AND TRADEMARK OFFICE
CERTIFICATE OF CORRECTION

PATENT NO. : 6,039,732
DATED : March 21, 2000
INVENTOR(S) : Yoshito Ichikawa et al It is certified that error appears in the above-identified patent and that said Letters Patent is hereby corrected as shown below:

Drawing,
Figure 18, at the end of the "Yes" arrow from the block "SET VALUE 5~5W", change "②" to -- ① --.

Signed and Sealed this

Thirteenth Day of November, 2001

Attest:

*Nicholas P. Godici*

NICHOLAS P. GODICI
*Attesting Officer*  *Acting Director of the United States Patent and Trademark Office*